United States Patent
Oshlack et al.

(10) Patent No.: US 6,743,442 B2
(45) Date of Patent: *Jun. 1, 2004

(54) MELT-EXTRUDED ORALLY ADMINISTRABLE OPIOID FORMULATIONS

(75) Inventors: Benjamin Oshlack, New York, NY (US); Mark Chasin, Manalapan, NJ (US); Hua-Pin Huang, Englewood Cliffs, NJ (US); David Sackler, Greenwich, CT (US)

(73) Assignee: Euro-Celtique, S.A., Luxembourg (LU)

( * ) Notice: Subject to any disclaimer, the term of this patent is extended or adjusted under 35 U.S.C. 154(b) by 0 days.

This patent is subject to a terminal disclaimer.

(21) Appl. No.: 09/777,616

(22) Filed: Feb. 6, 2001

(65) Prior Publication Data

US 2001/0036476 A1 Nov. 1, 2001

Related U.S. Application Data

(63) Continuation of application No. 09/360,056, filed on Jul. 23, 1999, now Pat. No. 6,261,599, which is a continuation of application No. 08/833,948, filed on Apr. 10, 1997, now Pat. No. 5,958,452, which is a continuation-in-part of application No. PCT/US95/14745, filed on Nov. 3, 1995, which is a continuation-in-part of application No. 08/334,209, filed on Nov. 4, 1994, now Pat. No. 5,965,161.

(51) Int. Cl.⁷ ............................. A61K 9/14; A61K 9/22; A61K 9/52

(52) U.S. Cl. ....................... 424/456; 424/457; 424/458; 424/468; 424/484

(58) Field of Search .............................. 424/456, 468, 424/469, 451, 457, 464, 489, 484, 485, 486, 488

(56) References Cited

U.S. PATENT DOCUMENTS

| 2,738,303 A | 3/1956 | Blythe et al. .................. 167/82 |
| 3,065,143 A | 11/1962 | Christenson et al. |
| 3,652,589 A | 3/1972 | Flick et al. ........... 260/326.5 M |
| 3,714,350 A | 1/1973 | Gough ........................ 424/203 |
| 3,830,934 A | 8/1974 | Flick et al. .................. 424/330 |

(List continued on next page.)

FOREIGN PATENT DOCUMENTS

| AU | 57224 | 5/1986 | .......... A61K/47/00 |
| AU | 8976091 | 6/1992 | .......... A23L/001/09 |
| CA | 2082573 | 5/1993 | .......... A61K/047/38 |
| CA | 2131350 A1 | 3/1995 | .......... A61K/31/135 |
| CA | 2150304 A1 | 12/1995 | .............. B01J/2/20 |

(List continued on next page.)

OTHER PUBLICATIONS

Nicolas Follonier1, Eric Doelker and Ewart T. Cole, *Evaluation of Hot–Melt Extrusion as a New Technique for the Production of Polymer–Based Pellets for Sustained Release Capsules containing high loadings of freely soluble drugs*, Drug Development and Industrial Pharmacy, 20(8), 1323–1339 (1994).

Nicolas Follonier[1], Eric Doelker[1] and Ewart T. Cole[2], *Hot–Melt Extruded Pellets for the Sustained Release of Highly Dosed Freely Solluble Drugs*, Proceed. Intern. Symp. COntrol. Rel. Bioact. Mater., 18(1991), pp. 578–579.

(List continued on next page.)

Primary Examiner—James M. Spear
(74) Attorney, Agent, or Firm—Davidson, Davidson & Kappel LLC

(57) ABSTRACT

Bioavailable sustained release oral opioid analgesic dosage forms, comprising a plurality of multiparticulates produced via melt extrusion techniques are disclosed.

34 Claims, 17 Drawing Sheets

U.S. PATENT DOCUMENTS

| | | | |
|---|---|---|---|
| 3,845,770 A | 11/1974 | Theeuwes et al. | 128/260 |
| 3,880,991 A | 4/1975 | Yolles | 424/22 |
| 3,950,508 A | 4/1976 | Mony et al. | 424/19 |
| 3,965,256 A | 6/1976 | Leslie | 424/22 |
| 3,974,157 A | 8/1976 | Shetty et al. | 260/247.2 B |
| 4,013,784 A | 3/1977 | Speiser | 424/19 |
| 4,076,798 A | 2/1978 | Casey et al. | 424/419 |
| 4,132,753 A | 1/1979 | Blichare et al. | 264/25 |
| 4,173,417 A | 11/1979 | Kruder | 366/89 |
| 4,230,687 A | 10/1980 | Sair et al. | 424/22 |
| 4,259,314 A | 3/1981 | Lowey | 424/19 |
| 4,265,875 A | 5/1981 | Byrne et al. | 424/19 |
| 4,292,300 A | 9/1981 | Byrne et al. | 424/19 |
| 4,310,483 A | 1/1982 | Dorfel et al. | 264/117 |
| 4,343,789 A | 8/1982 | Kawata et al. | 424/461 |
| 4,344,431 A | 8/1982 | Yolles | 128/260 |
| 4,346,709 A | 8/1982 | Schmitt | 128/260 |
| 4,366,172 A | 12/1982 | Lednicer | 424/330 |
| 4,374,082 A | 2/1983 | Hochschild | 264/129 |
| 4,380,534 A | 4/1983 | Fukui et al. | 264/38 |
| 4,389,393 A | 6/1983 | Schor et al. | 424/19 |
| 4,406,883 A | 9/1983 | Byrne et al. | 424/80 |
| 4,421,736 A | 12/1983 | Walters | 424/21 |
| 4,483,847 A | 11/1984 | Augart | 424/22 |
| 4,533,562 A | 8/1985 | Ikegami et al. | 427/3 |
| 4,613,619 A | 9/1986 | Sleigh et al. | 514/546 |
| 4,621,114 A | 11/1986 | Watanabe | 524/451 |
| 4,649,042 A | 3/1987 | Davis et al. | 424/419 |
| 4,720,384 A | 1/1988 | Di Luccio et al. | 424/78 |
| 4,764,378 A | 8/1988 | Keith et al. | 424/435 |
| 4,778,676 A | 10/1988 | Yang et al. | 424/79 |
| 4,801,458 A | 1/1989 | Hidaka et al. | 424/443 |
| 4,801,460 A | 1/1989 | Goertz et al. | 424/465 |
| 4,806,337 A | 2/1989 | Snipes et al. | 71/65 |
| 4,818,450 A | 4/1989 | Hall et al. | 264/39 |
| 4,828,836 A | 5/1989 | Elger et al. | 424/419 |
| 4,834,984 A | 5/1989 | Goldie et al. | 424/488 |
| 4,842,761 A | 6/1989 | Rutherford | 252/90 |
| 4,844,907 A | 7/1989 | Elger et al. | 424/465 |
| 4,844,909 A | 7/1989 | Goldie et al. | 424/480 |
| 4,861,598 A | 8/1989 | Oshlack | 424/468 |
| RE33,093 E | 10/1989 | Schiraldi et al. | 424/676 |
| 4,879,108 A | 11/1989 | Yang et al. | 424/440 |
| 4,880,585 A | 11/1989 | Klimesch et al. | 264/141 |
| 4,880,830 A | 11/1989 | Rhodes | 424/470 |
| 4,882,151 A | 11/1989 | Yang et al. | 424/440 |
| 4,882,152 A | 11/1989 | Yang et al. | 424/440 |
| 4,882,153 A | 11/1989 | Yang et al. | 424/440 |
| 4,882,155 A | 11/1989 | Yang et al. | 424/440 |
| 4,882,156 A | 11/1989 | Yang et al. | 424/440 |
| 4,882,157 A | 11/1989 | Yang et al. | 424/440 |
| 4,882,159 A | 11/1989 | Yang et al. | 424/440 |
| 4,882,167 A | 11/1989 | Jang | 424/468 |
| 4,894,234 A | 1/1990 | Sharma et al. | 424/440 |
| 4,917,899 A | 4/1990 | Geoghegan et al. | 424/19 |
| 4,925,675 A | 5/1990 | Giannini et al. | 424/19 |
| 4,935,246 A | 6/1990 | Ahrens | 424/490 |
| 4,957,681 A | 9/1990 | Klimesch et al. | 264/211.23 |
| 4,959,208 A | 9/1990 | Chakrabarti et al. | 424/78 |
| 4,967,486 A | 11/1990 | Doelling | 34/1 |
| 4,970,075 A | 11/1990 | Oshlack | 424/451 |
| 4,987,136 A | 1/1991 | Kreek et al. | |
| 4,990,341 A | 2/1991 | Goldie et al. | 424/484 |
| 4,992,100 A | 2/1991 | Koepff et al. | 106/125 S |
| 4,994,227 A | 2/1991 | Dietz et al. | 264/328.16 |
| 5,007,790 A | 4/1991 | Shell | 424/451 |
| 5,013,306 A | 5/1991 | Solomon et al. | 604/265 |
| 5,023,089 A | 6/1991 | Sakamoto et al. | 424/502 |
| 5,026,560 A | 6/1991 | Makino et al. | 424/494 |
| 5,030,400 A | 7/1991 | Danielsen et al. | 264/101 |
| 5,035,509 A | 7/1991 | Kruder | 366/89 |
| 5,049,394 A | 9/1991 | Howard et al. | 424/490 |
| 5,055,307 A | 10/1991 | Tsuru et al. | 424/693 |
| 5,073,379 A | 12/1991 | Klimesch et al. | 424/467 |
| 5,102,668 A | 4/1992 | Eichel et al. | 424/490 |
| 5,126,145 A | 6/1992 | Evenstad et al. | 424/465 |
| 5,132,142 A | 7/1992 | Jones et al. | 427/196 |
| 5,133,974 A | 7/1992 | Paradissis et al. | 424/480 |
| 5,162,117 A | 11/1992 | Stupak et al. | 424/475 |
| 5,165,952 A | 11/1992 | Solomon et al. | 427/2 |
| 5,167,964 A | 12/1992 | Muhammad et al. | 424/482 |
| 5,169,645 A | 12/1992 | Shukla et al. | 424/499 |
| 5,178,868 A | 1/1993 | Malmqvist-Granlund et al. | 424/490 |
| 5,183,690 A | 2/1993 | Carr et al. | 427/213.31 |
| 5,196,203 A | 3/1993 | Boehm | 424/490 |
| 5,202,128 A | 4/1993 | Morella et al. | 424/469 |
| 5,204,119 A | 4/1993 | Shiobara et al. | 424/489 |
| 5,229,148 A | 7/1993 | Copper | 426/5 |
| 5,234,697 A | 8/1993 | Sipos | 424/490 |
| 5,240,400 A | 8/1993 | Fujimoto et al. | 425/310 |
| 5,262,172 A | 11/1993 | Sipos | 424/490 |
| 5,266,331 A | 11/1993 | Oshlack et al. | 424/468 |
| 5,271,934 A | 12/1993 | Goldberg et al. | 424/401 |
| 5,273,758 A | 12/1993 | Royce | 424/465 |
| 5,283,065 A | 2/1994 | Doyon et al. | 424/467 |
| 5,290,560 A | 3/1994 | Autant et al. | 424/438 |
| 5,292,461 A | 3/1994 | Juch et al. | 264/37 |
| 5,296,266 A | 3/1994 | Kunugi et al. | 427/213 |
| 5,300,300 A | 4/1994 | Egidio et al. | 424/456 |
| 5,340,581 A | 8/1994 | Tseng et al. | 424/401 |
| 5,350,584 A | 9/1994 | McClelland et al. | 424/501 |
| 5,354,856 A | 10/1994 | Kawashima et al. | 536/127 |
| 5,356,635 A | 10/1994 | Raman et al. | 424/484 |
| 5,378,462 A | 1/1995 | Boedecker et al. | 424/94.29 |
| 5,380,535 A | 1/1995 | Geyer et al. | 424/484 |
| 5,395,626 A | 3/1995 | Kotwal et al. | 424/472 |
| 5,403,593 A | 4/1995 | Royce | 424/489 |
| 5,443,846 A | 8/1995 | Yoshioka et al. | 424/498 |
| 5,451,424 A | 9/1995 | Solomon et al. | 427/2.1 |
| 5,453,283 A | 9/1995 | Munch et al. | 424/489 |
| 5,456,923 A | 10/1995 | Nakamichi et al. | 424/489 |
| 5,472,710 A | 12/1995 | Klokkers-Bethke et al. | 424/468 |
| 5,476,528 A | 12/1995 | Trimm et al. | 71/21 |
| 5,478,577 A | 12/1995 | Sackler et al. | |
| 5,510,114 A | 4/1996 | Borella et al. | 424/452 |
| 5,516,205 A | 5/1996 | Oda et al. | 366/75 |
| 5,552,159 A | 9/1996 | Mueller et al. | 424/464 |
| 5,567,439 A | 10/1996 | Myers et al. | 424/486 |
| 5,700,410 A | 12/1997 | Nakamichi et al. | 264/122 |
| 5,958,452 A * | 9/1999 | Oshlack et al. | 424/457 |

FOREIGN PATENT DOCUMENTS

| | | | |
|---|---|---|---|
| DE | 2439538 | 3/1976 | A61K/9/22 |
| DE | 3602360 A1 | 7/1987 | B65G/65/06 |
| DE | 3602370 A1 | 8/1987 | A61K/45/06 |
| DE | 3623193 A1 | 1/1988 | A61K/31/205 |
| DE | 4329794 A1 | 3/1995 | A61K/31/135 |
| EP | 0032004 A | 12/1980 | A61K/9/22 |
| EP | 0097523 A2 | 8/1983 | A61K/9/26 |
| EP | 0043254 B1 | 5/1984 | A61K/9/26 |
| EP | 0108218 A2 | 5/1984 | A61K/9/22 |
| EP | 0147780 A2 | 12/1984 | A61K/9/32 |
| EP | 0152379 A2 | 8/1985 | A61K/9/50 |
| EP | 0214735 A2 | 7/1986 | A61K/9/22 |
| EP | 0189861 A2 | 8/1986 | A61K/47/00 |
| EP | 204596 | 12/1986 | A61K/9/14 |
| EP | 02 04596 A1 | 12/1986 | A61K/9/16 |
| EP | 02 08144 A1 | 1/1987 | A61K/9/16 |
| EP | 0248548 A2 | 5/1987 | A61K/9/22 |
| EP | 0249347 A2 | 5/1987 | A61K/31/485 |

| | | | | | | | | |
|---|---|---|---|---|---|---|---|---|
| EP | 0251459 | A2 | 5/1987 | ............ A61K/9/22 | GB | 2117239 A | 3/1983 | ............ A61K/9/20 |
| EP | 0253104 | A1 | 6/1987 | ............ A61K/9/00 | GB | 2053681 B | 4/1984 | ............ A61K/9/22 |
| EP | 0240904 | | 10/1987 | ............ A61K/9/20 | GB | 2196848 A | 5/1988 | ............ A61K/9/22 |
| EP | 0240906 | A2 | 10/1987 | ............ A61J/3/10 | GB | 2207355 B | 1/1991 | .......... A61M/31/00 |
| EP | 0254978 | A1 | 2/1988 | ............ A61K/9/22 | GB | 2246514 A | 2/1992 | ............ A61K/9/16 |
| EP | 0256127 | B1 | 2/1988 | ............ C12N/9/00 | GB | 2281204 A | 3/1995 | ............ A61K/9/16 |
| EP | 0267702 | A2 | 5/1988 | ............ A61K/9/14 | GB | 2284760 A | 6/1995 | ............ A61K/9/16 |
| EP | 0271193 | A2 | 6/1988 | ........ A61K/31/485 | JP | 5257315 | 5/1977 | ............ A61K/9/22 |
| EP | 0275834 | A1 | 7/1988 | ............ A61K/9/20 | JP | 2223513 | 9/1990 | ............ A61K/9/10 |
| EP | 0300897 | A2 | 7/1988 | ............ A61K/9/22 | JP | 2223533 | 9/1990 | .......... A61K/47/14 |
| EP | 0021129 | B2 | 9/1988 | ............ A61K/9/16 | WO | 9104015 | 4/1991 | ............ A61K/9/16 |
| EP | 0295212 | A2 | 12/1988 | .......... A61K/47/00 | WO | 9119484 | 12/1991 | ............ A61K/9/16 |
| EP | 0327295 | A2 | 8/1989 | ............ A61K/9/52 | WO | 9119485 | 12/1991 | ............ A61K/9/16 |
| EP | 0337256 | A2 | 10/1989 | ............ A61K/9/20 | WO | 9201446 | 2/1992 | ............ A61K/9/50 |
| EP | 0068450 | B1 | 1/1990 | ............ A61K/9/20 | WO | 9202209 | 2/1992 | ............ A61K/9/22 |
| EP | 0351580 | A2 | 1/1990 | ............ A61K/9/22 | WO | 9205774 | 4/1992 | ............ A61K/9/18 |
| EP | 0377518 | A2 | 1/1990 | ............ A61K/9/52 | WO | 9206679 | 4/1992 | ............ A61K/9/16 |
| EP | 0354345 | A2 | 2/1990 | ............ C09H/9/04 | WO | 9218106 | 10/1992 | ............ A61K/9/14 |
| EP | 0358105 | A2 | 3/1990 | ............. A61J/3/10 | WO | 9222283 | 12/1992 | ............ A61K/9/02 |
| EP | 0358107 | A2 | 3/1990 | ............ A61K/9/20 | WO | 9300063 | 1/1993 | ............. A61J/3/00 |
| EP | 0361680 | B1 | 4/1990 | ............ A61K/9/46 | WO | 9300076 | 1/1993 | ............ A61K/9/51 |
| EP | 0361910 | A1 | 4/1990 | ............ A61K/9/16 | WO | 9304675 | 3/1993 | .......... A61K/31/16 |
| EP | 0368247 | A2 | 5/1990 | ............ A61K/9/26 | WO | 9307859 | 4/1993 | ............ A61K/9/16 |
| EP | 0375063 | A1 | 6/1990 | ............ A61K/9/18 | WO | WO 9307859 | 4/1993 | ............ A61K/9/16 |
| EP | 0377517 | A2 | 7/1990 | ......... A61K/31/52 | WO | 9307861 | 4/1993 | ............ A61K/9/50 |
| EP | 0298355 | B1 | 11/1990 | ............ A61K/9/50 | WO | 9310765 | 6/1993 | ............ A61K/9/22 |
| EP | 0415693 | A1 | 3/1991 | ......... A61K/37/02 | WO | 9317667 | 9/1993 | ............ A61K/9/16 |
| EP | 0430287 | B1 | 6/1991 | ............ A61K/9/54 | WO | 9318753 | 9/1993 | ............ A61K/9/16 |
| EP | 0463833 | A2 | 6/1991 | ............ A61K/9/26 | WO | WO 9324110 | 12/1993 | ............ A61K/9/20 |
| EP | 0241615 | B1 | 9/1991 | ............ A61K/9/22 | WO | 9324110 | 12/1993 | ............ A61K/9/20 |
| EP | 0452145 | A2 | 10/1991 | ............ A61K/9/14 | WO | 9403160 | 2/1994 | ............ A61K/9/32 |
| EP | 0239983 | B1 | 11/1991 | ............. A61J/3/06 | WO | 9403161 | 2/1994 | ............ A61K/9/52 |
| EP | 0465338 | | 1/1992 | ............ A61K/9/16 | WO | 9405262 | 3/1994 | ............ A61K/9/16 |
| EP | 0481600 | A2 | 4/1992 | .......... A61L/15/28 | WO | WO 9408568 | 4/1994 | ............ A61K/9/26 |
| EP | 0531611 | A1 | 4/1992 | ............ A61K/9/02 | WO | 9422431 | 10/1994 | ............ A61K/9/20 |
| EP | 0240904 | B1 | 7/1992 | ............ A61K/9/20 | WO | WO 9423698 | 10/1994 | ............ A61K/9/14 |
| EP | 0535841 | A1 | 9/1992 | ........ A61K/31/485 | WO | 9423700 | 10/1994 | ............ A61K/9/16 |
| EP | 0320480 | B1 | 11/1992 | ............ B01F/5/22 | WO | 9514460 | 6/1995 | ............ A61K/9/14 |
| EP | 0337256 | | 11/1992 | ............ A61K/9/20 | | | | |
| EP | 0526862 | A1 | 2/1993 | ............ A61K/9/20 | | | | |
| EP | 0338383 | B1 | 3/1993 | ............ A61K/9/54 | | | | |
| EP | 0529396 | | 3/1993 | ............ A61K/9/20 | | | | |
| EP | 0533297 | A1 | 3/1993 | ............ A61K/9/46 | | | | |
| EP | 0534628 | A1 | 3/1993 | ........ A61K/31/485 | | | | |
| EP | 0544144 | A1 | 6/1993 | ............ A61K/9/20 | | | | |
| EP | 0546676 | A1 | 6/1993 | .......... A61K/31/60 | | | | |
| EP | 06 67065 | A1 | 8/1993 | ............ A61K/9/16 | | | | |
| EP | 665010 | A1 | 10/1993 | ............ A61K/9/26 | | | | |
| EP | 0574894 | A1 | 12/1993 | ........ A61K/31/575 | | | | |
| EP | 580860 | A1 | 2/1994 | | | | | |
| EP | 0580860 | A1 | 2/1994 | ............ A61K/9/14 | | | | |
| EP | 0582380 | A1 | 2/1994 | ............. B01J/2/16 | | | | |
| EP | 0624366 | | 4/1994 | ......... A61K/31/135 | | | | |
| EP | 0595311 | A1 | 5/1994 | .......... A61K/31/44 | | | | |
| EP | 0249347 | B1 | 6/1994 | ........ A61K/31/485 | | | | |
| EP | 0436786 | B1 | 6/1994 | .......... B30B/11/22 | | | | |
| EP | 0636370 | A1 | 2/1995 | ........ A61K/31/485 | | | | |
| EP | 0491238 | B1 | 3/1995 | .......... B30B/11/22 | | | | |
| EP | 0642788 | A2 | 3/1995 | ......... A61K/31/135 | | | | |
| EP | 0609961 | A1 | 8/1995 | ........ A61K/31/485 | | | | |
| EP | 0205282 | B1 | 9/1995 | ............ A61K/9/22 | | | | |
| EP | 0624366 | B1 | 5/1996 | ......... A61K/31/135 | | | | |
| FR | 2273512 | | 1/1976 | ............. A61J/3/06 | | | | |
| FR | 2273584 | | 1/1976 | .............. B01J/2/10 | | | | |
| FR | 2642420 | A1 | 3/1990 | .......... C07C/55/10 | | | | |
| GB | 0997399 | | 4/1964 | | | | | |
| GB | 1405088 | | 6/1971 | ............ A61K/9/26 | | | | |
| GB | 1504553 | | 3/1978 | .......... A61K/47/00 | | | | |
| GB | 1513166 | | 6/1978 | .............. B29B/1/02 | | | | |
| GB | 2030861 | A | 4/1980 | ............. A61J/3/08 | | | | |
| GB | 2111386 | A | 12/1982 | ............ A61K/9/20 | | | | |

OTHER PUBLICATIONS

*Twin Screw Extrusion in the Production of Novel Dosage Forms*, Pharmaceutical Manufacturing Review (Jun. 1994).

Follonier, Nicolas, et al., "Hot–Melt Extruded Pellets for The Sustained Release of Highly Dosed Freely Soluble Drugs", *Capsule News*, vol. 1, No. 3, Edited by Roland Daumesnil, (Jun./Jul. 1991).

Frank W. Goodhart et al., Design and Use of a Laboratory Extruder for Pharmaceutical Granulations, Journal of Pharm. Scien., 62(1), pp. 133–136 (Jan. 1973).

Publication, KEX, Twin Screw Compounding Extruder, (Oct. 1989).

Abstract No. 2–223533 "Agent with Release–Controlled Matrix" no date available.

Derwent Abstract DE 2553026 (1976).

Derwent Abstract of JP 62040277 (1987).

Derwent Abstract of JP58109411 (1983).

Derwent Abstract EP 358 107 (1990).

Sekiguchi, et al., "Studies on Absorption of Eutectic Mixture . . . ", Chem. Pharm. Bull., vol. 9 (1961), pp. 866–872.

A.R. Gennaro, "Particle Phenomena and Coarse Dispersions", Remington's Pharmaceutical Sciences, 17th Edition, 1985, p. 301.

J.L. Ford, "The Current Status of Solid Dispersions", Pharm. Acta Helv. 61, Nr. 3 (1986), pp. 69–88.

CA 74:67660 (1996) (1 page).

CA 101:60081 (1996) (1 page).

CA 113:98975 (1996) (1 page).

CA 113:218240 (1996) (1 page).
CA 114:30199 (1996) (1 page).
CA 112:75438 (1996) (1 page).
CA 115:177364 (1997) (1 page).
R. Kinget, et al., "Preparation and Properties of Granulates Containing Solid Dispersions", Acta Phar. Tech., vol. 31, No. 2, 1985, pp. 57–62.
M.J. Jozwiakowski et al., "Characterization of a Hot–Melt Fluid Bed Coating Process for Fine Granules", Pharm. Research, vol. 7, No. 11, 1990, pp. 1119–1124.
B. Evrard et al., "Melt Granulation with a New Laboratory High–Shear Mixer", Laboratoire de Pharmacie Galenique, Institut de Pharmacie, No Date Available.
M. Niskanen et al., "Pelletization in a Centrifugal Granulator, Part I: Effects of Binder–Solution Concentration", Pharm. Tech. Int'l., Oct. 1990, pp. 22–38.
L. Lachman et al., "The Theory and Practice of Industrial Pharmacy", p. 315, Lea & Febiger, Phi. 1976.
FDA Guide to Inspections of Oral Solid Dosage Forms Pre/Post Approval Issues for Development and Validation, Jan. 1994.
T. Schaefer et al., "Melt Pelletization in a High Shear Mixer I Effects of Process Variables and Binder", Acta Pharm. Nord. vol. 4, No. 3, pp. 133–140, 1992.
T. Schaefer et al., "Melt Pelletization in a High Shear Mixer II Power Consumption and Granule Growth", Acta Pharm. Nord. vol. 4, No. 3, pp. 141–148, 1992.
T. Schaefer, et al., "Melt Granulation in a Laboratory Scale High Shear Mixer", Drug Dev. and Indust. Phar., vol. 16, No. 8, pp. 1249–1277, 1990.
McTaggart, C.M. et al., "The Evaluation of Formulation and Processing Conditions of a Melt Granulation Process", Int'L. J. Pharm. vol. 19, No. 2, issued 1984, pp. 139–148.
El–Shanawany, S., "Sustained Release of Nitrofurantion From Inert Wax Matrixes", J. Controlled Release, vol. 26, No. 1, issued 1993, pp. 11–19.
P. Flanders, et al., "The Control of Drug Releases From Conventional Melt Granulation Matrices", Drug Dev. and Industrial Pharm., vol. 13, No. 6, pp. 1001–1022, 1987.
Thomsen, L. Juul, "Matrix Pellets Prolonged Formulations Prepared by Melt Pelletization", Dept. of Pharm. Royal Danish School of Pharmacy, 1992.
Thomsen, L. Juul, et al., "Prolonged Release Matrix Pellets Prepared by Melt Pelletization I. Process Variables", Drug Development and Industrial Pharmac y, vol. 19, No. 15, pp. 1867–1887 (1993).
Thomsen, L. Juul, et al., "Prolonged Release Matrix Pellets Prepared by Melt Pelletization II. Hydrophobic Substances as Meltable Binders", Drug Development and Industrial Pharmacy, vol. 20, No. 7, pp. 1179–1197 (1994).
Thomsen, L. Juul, "Utilizing melt pelletization tequnique for the preparation of prolonged release products", Pelletization, (material elaborated by assistant Prof. Lars Juul Thomsen, Dept. of Pharmaceutics, Royal Danish School of Pharmacy for the DIE course "Pelletization Technology", Nov. 1992, 106 pages plus appendixes.
Thomsen, L. Juul, "Prolonged Release Matrix Pellets Prepared by Melt Pelletization. Part IV: Drug Content, Drug Particle Size and Binder Composition", Pharmaceutical Technology Europa, pp. 19–22 (Oct. 1994).

N. Follonier et al., "Evaluation of Hot–Melt Extrusion as a New Technique for the Production of Polymer–Based Pellets for Sustained Release Capsules Containing High Loadings of Freely Soluble Drugs", Drug. Dev. and Industr. Pharm., vol. 20, No. 8, pp. 1323–1339, (1994).
Sustained Release Medications, pp. 50–53, Noyes Data Corp. (J.C. Johnson), 1980.
M.A. Longer, "Sustained–Release Drug Deliver Systems", Remington's Pharm. Scie., 18th Edition, pp. 1676–1693, 1990.
M. Zahirul I. Khan, "Recent Trends and Progress in Sustained or Controlled Oral Delivery of Some Water Soluble Drugs: Morphine Salts, Diltiazem and Captopril", Drug Devl. and Industr. Pharm., vol. 21, No. 9, pp. 1037–1070, 1995.
J.P. Skelly, Scael–up of Immediate Releae Oral Solid Dosage Forms, AAPS/FDA Workshop Committee, Pharmaceutical Technology, pp. 68–74, Apr. 1995.
SK Baveja et al., Int. J. Pharmaceutics, 41, (1988), pp. 55–62.
Formulating for Controlled Release with METHOCEL® Premium Cellulose Ethers, The Dow Chemical Company, 1989.
M.S. Vazquez et al., Ddrug Dev. & Ind. Pharmacy, 18 (11 & 12), pp. 1355–1378 (1992).
L W S Cheong et al., Pharm. Res. 9(11), pp. 1510–1514 (1992).
Hunt et al., Clin. Ther., vol. 13, No. 4, pp. 482–488, 1990.
METHOCEL, Colorcon. Technical Information No Date Available.
DA Alderman, Int. J. Pharm. Tech. and Prod. Mfr., 5(3), pp. 1–9, 1984.
HE Huber et al., J. Pharm. Sci. 55 (9), Sep. 1966, pp. 974–976.
Lin SY et al., Current Therapeutic Research 52 (3), pp. 486–492, Sep., 1992.
Aqualon Technical Information Bulletin, VC–585, 1991.
P. Colombo, Advanced Drug Delivery Reviews, 11 (1993), pp. 37–57.
KV Ranga Rao et al., Int. J. Pharmaceutics, 48 (1988), pp. 1–13.
JE Hogan, Drug Dev. & Ind. Pharmacy, 15 (6 & 7), pp. 975–999, (1989).
JL Ford et al., Int. J. Pharmaceutics, 24 (1985), pp. 327–338.
PB Daly et al., Int. J. Pharmaceutics, 18 (1984), pp. 201–205.
E.M.G. van Bommel, "Production and Evaluation of in Vitro Release Characteristics of Spherical Grandient Matrix Systems", Acta Phar., Technol. 3b (2), pp. 74–78, 1990.
Nicolas Follonier et al., "Various Ways of Modulating the Release of Diltiazem Hydrochloride from Hot–melt Extruded Sustained Release Pellets Prepard Using Polymeric Materials", Journal of Controlled Release, 36, pp. 243–250 (1995).
Alan Royce et al., "Alternative Granulation Technique: Melt Granulation", Drug Development and Industrial Pharmacy, 22 (9 & 10), pp. 917–992 (1996).
Derwent Abstract of EP 0208144, published Jan. 14, 1987.
English translation of Japanese text of J. L. White, *Twin Screw Extrusion, Technology and Principles,* pp. 14 and 37, 1981.

* cited by examiner

MELT-EXTRUDED ORALLY ADMINISTRABLE OPIOID FORMULATIONS

This application is a continuation of U.S. patent application Ser. No. 09/360,056, filed Jul. 23, 1999, U.S. Pat. No. 6,261,599 which is a continuation of U.S. patent application Ser. No. 08/833,948, filed Apr. 10, 1997, now U.S. Pat. No. 5,958,452, which is a continuation-in-part of PCT/US95/14745, filed Nov. 3, 1995, which is a continuation-in-part of U.S. patent application Ser. No. 08/334,209, filed Nov. 4, 1994, now U.S. Pat. No. 5,965,161, the disclosures of which are all hereby incorporated by reference in their entirety.

BACKGROUND OF THE INVENTION

The present invention relates to the use of melt extrusion technology in the production of bioavailable sustained-release matrix pharmaceutical formulations. Previously, melt extrusion has been used in the production of immediate release formulations.

It is known in the pharmaceutical art to prepare compositions which provide for controlled release of pharmacologically active substances contained in the compositions after oral administration to humans and animals. Such slow release compositions are used to delay absorption of a medicament until it has reached certain portions of the alimentary tract. Such sustained-release of a medicament in the alimentary tract further maintains a desired concentration of said medicament in the blood stream for a longer duration than would occur if conventional rapid release dosage forms are administered.

Different methods of preparing controlled release pharmaceutical dosage forms have been suggested. For example, direct compression techniques, wet granulation techniques, encapsulation techniques and the like have been proposed to deliver pharmaceutically active ingredients to the alimentary tract over extended periods.

Additionally, various types of sustained release formulations are known in the art, including specially coated pellets, coated tablets and capsules wherein the slow release of the active medicament is brought about through selective breakdown of the coating of the preparation or through compounding with a special matrix to affect the release of a drug. Some sustained release formulations provide for related sequential release of a single dose of an active compound at predetermined periods after administration.

It is the intent of all sustained-release preparations to provide a longer period of pharmacologic response after the administration of the drug and is ordinarily experienced after the administration of the rapid release dosage forms. Such longer periods of response provide for many inherent therapeutic benefits that are not achieved with corresponding short acting, immediate release preparations. This is especially true in the treatment of cancer patients or other patients in need of treatment for the alleviation of moderate to severe pain, where blood levels of an opioid analgesic medicament must be maintained at a therapeutically effective level to provide pain relief. Unless conventional rapid acting drug therapy is carefully administered at frequent intervals to maintain effective steady state blood levels of the drug, peaks and valleys in the blood level of the active drug occur because of the rapid absorption, systemic excretion of the compound and through metabolic inactivation, thereby producing special problems in maintenance of analgesic efficacy.

The prior art teaching of the preparation and use of compositions providing the sustained-release of an active compound from a carrier is basically concerned with the release of the active substance into the physiological fluid of the alimentary tract. However, it is generally recognized that the mere presence of an active substance in the gastrointestinal fluids does not, by itself, insure bioavailablity.

In order to be absorbed, the active drug substance must be in solution. The time required for a given proportion of an active substance from a unit dosage form is determined as the proportion of the amount of active drug substance release from a unit dosage form over a specified time base by a test method conducted under standardized conditions. The physiological fluids of the gastrointestinal tract are the media for determining dissolution time. The present state of the art recognizes many satisfactory test procedures to measure dissolution time for pharmaceutical compositions, and these test procedures are described in official compendia world wide.

Although there are many diverse factors which influence the dissolution of drug substance from its carrier, the dissolution time determined for a pharmacologically active substance form the specific composition is relatively constant and reproducible. Among the different factors affecting the dissolution time are the surface area of the drug substance presented to the dissolution solvent medium, the pH of the solution, the solubility of the substance in the specific solvent medium, and the driving forces of the saturation concentration of dissolved materials in the solvent medium. Thus, the dissolution concentration of an active drug substance is dynamically modified in its steady state as components are removed from the dissolution medium through absorption across the tissue site. Under physiological conditions, the saturation level of the dissolved materials is replenished form the dosage form reserve to maintain a relatively uniform and constant dissolution concentration in the solvent medium providing for a steady state absorption.

The transport across a tissue absorption site of the gastrointestinal tract is influenced by the Donnan osmotic equilibrium forces on both sides of the membrane since the direction of the driving force is the difference between the concentrations of active substance on either side of the membrane, i.e., the amount dissolved in the gastrointestinal fluids and the amount present in the blood. Since the blood levels are constantly being modified by dilution, circulatory changes, tissue storage, metabolic conversion and systemic excretion, the flow of active materials is directed from the gastrointestinal tract into the blood stream.

Notwithstanding the diverse factors influencing both dissolution and absorption of a drug substance, a strong correlation has been established between the in-vitro dissolution time determined for a dosage form and (in-vivo) bioavailablity. The dissolution time and the bioavailablity determined for a composition are two of the most significant fundamental characteristics for consideration when evaluating sustained-release compositions.

Metal granulations techniques have also been suggested to provide controlled release formulations. Generally, melt granulation involves mechanically working an active ingredient in particulate form with one or more suitable binders and/or pharmaceutically acceptable excipients in a mixer until one or more of the binders melts and adheres to the surface of the particulate, eventually building up granules.

U.S. Pat. No. 4,957,681 (Klimesch, et. al.) discloses a continuous process for preparing pharmaceutical mixtures having at least two components which are continuously metered. The process includes continuously metering the individual components of the pharmaceutical mixture at a rate of at least 50 g/h on electronic differential metering balances having a metering accuracy of at least ±5% within time intervals of less than one minute and, additionally, having screw conveyors, thereby obtaining a substantially uniformly metered mixture; and shaping the mixture. Example 1 of the '681 patent is representative of the process. The requisite amounts of a copolymer having a K value of 30 and obtained from 60% of N-vinylpyrrolid-2-one (NVP), stearyl alcohol and theophylline are metered via three metering balances into the hopper of an extruder and extruded. The temperatures of the extruder cylinder consisting of six shots ranged form 30–60° C. and the die is heated to 100° C. The resultant extrudate is then pressed into tablets of the required shape. The '681 patent does not disclose preparation of sustained release opioid pharmaceutical formulations.

N. Follonier., et al., *Hot-Melt Extruded Pellets for the Sustained Release of Highly Dosed Freely Soluble Drugs*, Proceed. Intern. Symp. Control. Rel. Bioact. Mater., 18 (1991) described certain diltiazem hydrochloride formulations prepared using hot-melt screw-extrusion to obtain sustained-release pellets to be filled into hard gelatin capsules. The polymers used were ethylcellulose, a copolymer of ethyl acrylate and methyl methacrylate containing quaternary ammonium groups, cellulose acetate butyrate, poly (vinyl chloride-co-vinyl acetate) and a copolymer of ethylene and vinyl acetate. In order to lower the extrusion temperature, some plasticizers were used.

WO 93/07859 describes drug loaded pellets produced through melt spheronization wherein the therapeutically active agent is blended with various excipients and binders; the formulation is fed to an extruder where it is heated and extruded at a speed of about 0.05 to 10 mm/sec. at approximately 60–180° C. The extrudate is then cut into pieces in a pelletizer and subsequently fed to a spheronizer for uniform pellet formulation.

Despite the foregoing advances and the various techniques for preparing sustained release formulations available in the pharmaceutical art, there is a need in the art for an orally administrable opioid formulation which would provide an extended duration of effect which is also easy to prepare, e.g via melt-granulation techniques.

OBJECTS AND SUMMARY OF THE INVENTION

It is therefore an object of the present invention to provide sustained-release pharmaceutical formulations suitable for oral administration and methods for preparing the same utilizing melt-extrusion techniques.

It is also an object of the present invention to provide improved methods for producing pharmaceutical extrudates containing opioid analgesics and pharmaceutical acceptable hydrophobic materials via melt extrusion techniques.

It is a further object of the present invention to provide a sustained-release melt extruded multi-particulate formulation which need not be spheronized in order to obtain a final dosage form.

It is also an object of the present invention to provide methods of treatment for human patients in need of opioid analgesic therapy using dosage forms prepared in accordance with the methods disclosed herein.

In accordance with the above objects and others which will be apparent from the further reading of the specification and of the appended claims, the present invention is related in part to the surprising discovery that sustained-release oral opioid analgesic formulations may be prepared utilizing melt extrusion techniques to provide bioavailable unit dose products which provide analgesic in a patient for, e.g., 8–24 hours.

The invention is also related in part to a new melt-extruded oral sustained-release dosage forms which comprise a pharmaceutically acceptable hydrophobic material, a retardant selected from waxes, fatty alcohols, and fatty acids, and a drug.

More particularly, one aspect of the present invention is related to a pharmaceutical extrudate including an opioid analgesic dispersed in a matrix. Preferably, the extrudate is strand or spaghetti-shaped and has diameter from about 0.1 to about 5 mm. The extrudate is divided into unit doses of the opioid analgesic for oral administration to a patient, and provides a sustained analgesic effect for 8–24 hours or more.

The matrices preferably include a hydrophobic material and a second retardant material (preferably a hydrophobic fusible carrier) which acts to further slow or control the release of the therapeutically active agent which the formulation is exposed to aqueous solution in-vitro, or exposed to gastic and/or intestinal fluids.

Preferably, the hydrophobic material is selected from the group consisting of alkylcelluloses, acrylic and methacrylic acid polymers and copolymers, shellac, zein, hydrogenated castor oil or hydrogenated vegetable oil, or mixtures thereof.

The retardant material (hydrophobic fusible carrier) is preferably selected from natural and synthetic waves, fatty acids, fatty alcohols and mixtures of the same. Examples include beeswax and carnauba wax, stearic acid, and stearyl alcohol. This list is of course not meant to be exclusive.

The extrudate may be cut into multiparticulates by any cutting means known in the art. Preferably, the multiparticulates have a length of from about 0.1 to 5 mm in length. The multiparticulates may then be divided into unit doses such that each individual unit dose includes a dose of opioid analgesic sufficient to provide analgesia to a mammal, preferably a human patient.

The unit doses of multiparticulates may then be incorporated into a solid pharmaceutical dosage formulation, e.g. via compression or shaping into tablets, by placing a requisite amount inside a gelatin capsule, or by forming the extruded product into the form of a suppository.

The pharmaceutical extrudates of the present invention may be prepared by blending the drug together with all matrix ingredients (hydrophobic material, binder and any additional (optional) excipients), feeding the resultant mixture into an extruder heated to the requisite temperature necessary to soften the mixture sufficiently to render the mixture extrudable; extruding the viscous, heated mass as a spaghetti-like strand; allowing the extrudate to congeal and harden, and then dividing the strand into desired pieces. This may be accomplished, e.g., by cutting the strands into pellets of 1.5 mm in diameter and 1.5 mm in length. Preferably, the extrudate has a diameter of from about 0.1 and 5 mm and provides sustained release of said opioid analgesic for a time period of from about 8 to about 24 hours.

Another aspect of the invention is directed to pharmaceutical dosage forms including the extrudate prepared as outlined above. The extrudate is cut into multiparticulates using any cutting means known in the art, e.g a blade. The multiparticulates are then divided into unit doses containing an effective amount of opioid analgesic to provide analgesia or pain relief in a human patient over the desired. dosing interval. The unit dose of multiparticulates may then be incorporated into tablets, e.g. via direct compression, formed into suppositories, or encapsulated by any means known in the art.

In yet a further aspect of the invention, there is provided a method of treating a patient with sustained-release formulations prepared as described above. This method includes administering a dosage form containing the novel extrudate to a patient in need of opioid analgesic therapy. For purposes of the present invention, a unit dose is understood to contain an effective amount of the therapeutically active agent to produce pain relief and/or analgesia to the patient. One skilled in the art will recognize that the dose of opioid analgesic administered to a patient will vary due to numerous factors; e.g. the specific opioid analgesic(s) being administered, the weight and tolerance of the patient, other therapeutic agents concomitantly being administered, etc.

As mentioned above, in order for a dosage form to be effective for its intended purpose, the dosage form must be bioavailable. For purposes of the present invention, the term "bioavailable" is defined as the total amount of a drug substance that is absorbed and available to provide the desired therapeutic effect after administration of a unit dosage form. Generally, the bioavailablity of a given dosage form is determined by comparison to a known reference drug product, as commonly determined and accepted by Governmental Regulatory Agencies, such as the United States FDA.

The term "bioavailabity" is defined for purposes of the present invention as the extent to which the drug (e.g., opioid analgesic) is absorbed from the unit dosage form and is available at the side of drug action.

The terms "sustained release", "extended duration", and "controlled release" are defined for purposes of the present invention as the release of the drug (e.g., opioid analgesic) at such a rate that blood (e.g., plasma) levels are maintained within the therapeutic range but below toxic levels over a period of time greater than 8 hours, more preferably for about 12 to about 24 hours, or longer.

The term "unit dose" is defined for purposes of the present invention as the total amount of multiparticulates needed to administered a desired dose of therapeutically active agent (e.g., opioid analgesic) to a patient.

The extrudates of the present invention preferably permit release of the opioid (or salts thereof) over a sustained period of time in an aqueous medium. The term "aqueous medium" is defined for purposes of the present invention as any water-containing medium, e.g. water, pharmaceutically acceptable dissolution medium, gastric fluid and/or intestinal fluid and the like.

BRIEF DESCRIPTION OF THE DRAWINGS

The following drawing is illustrative of an embodiment of the invention and is not means to limit the scope of the invention as encompassed by the claims.

DETAILED DESCRIPTION

Figure 1:
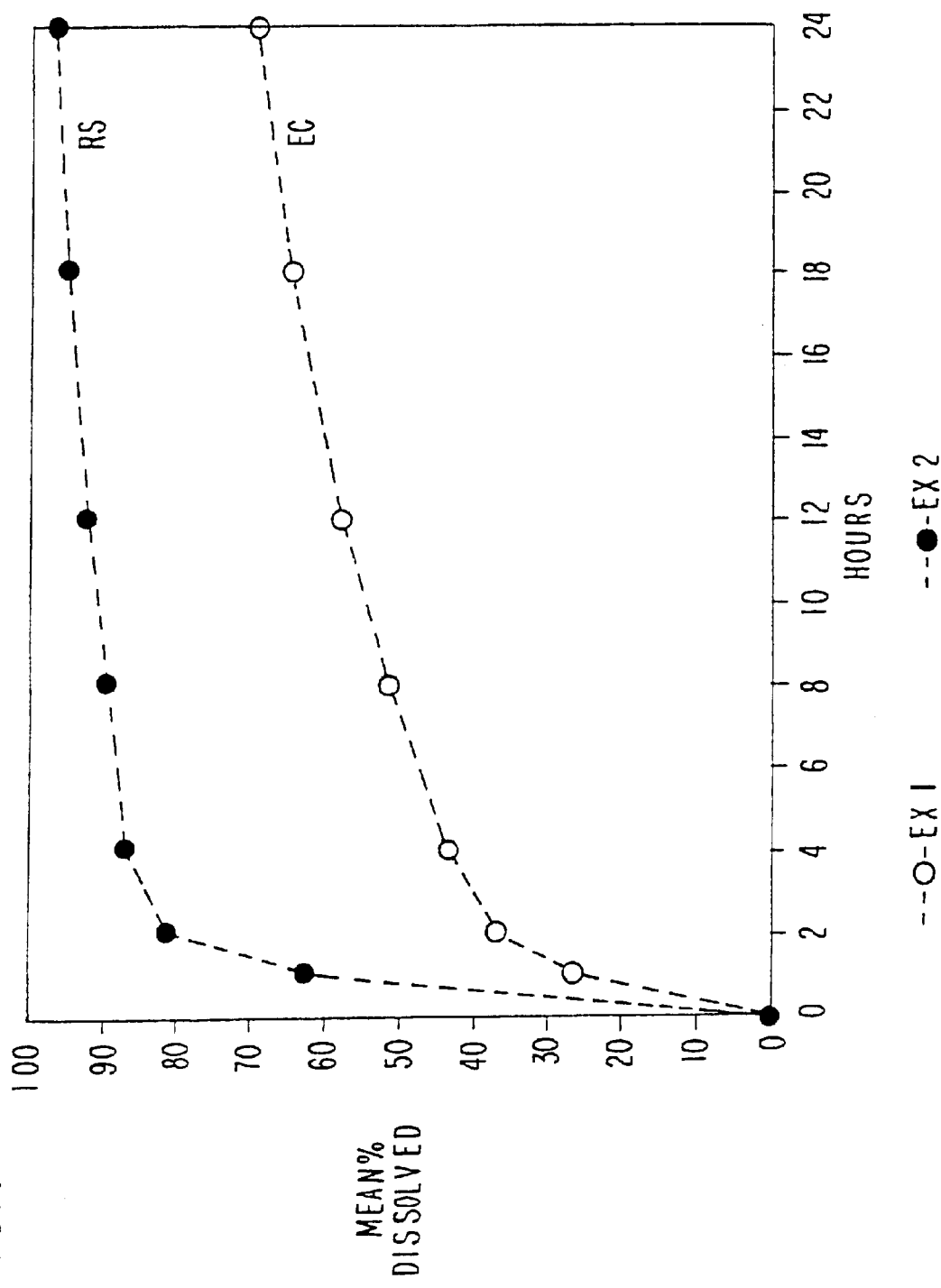
FIG. 1 is a graph displaying the dissolution results of Examples 1 and 2.
Figure 2:
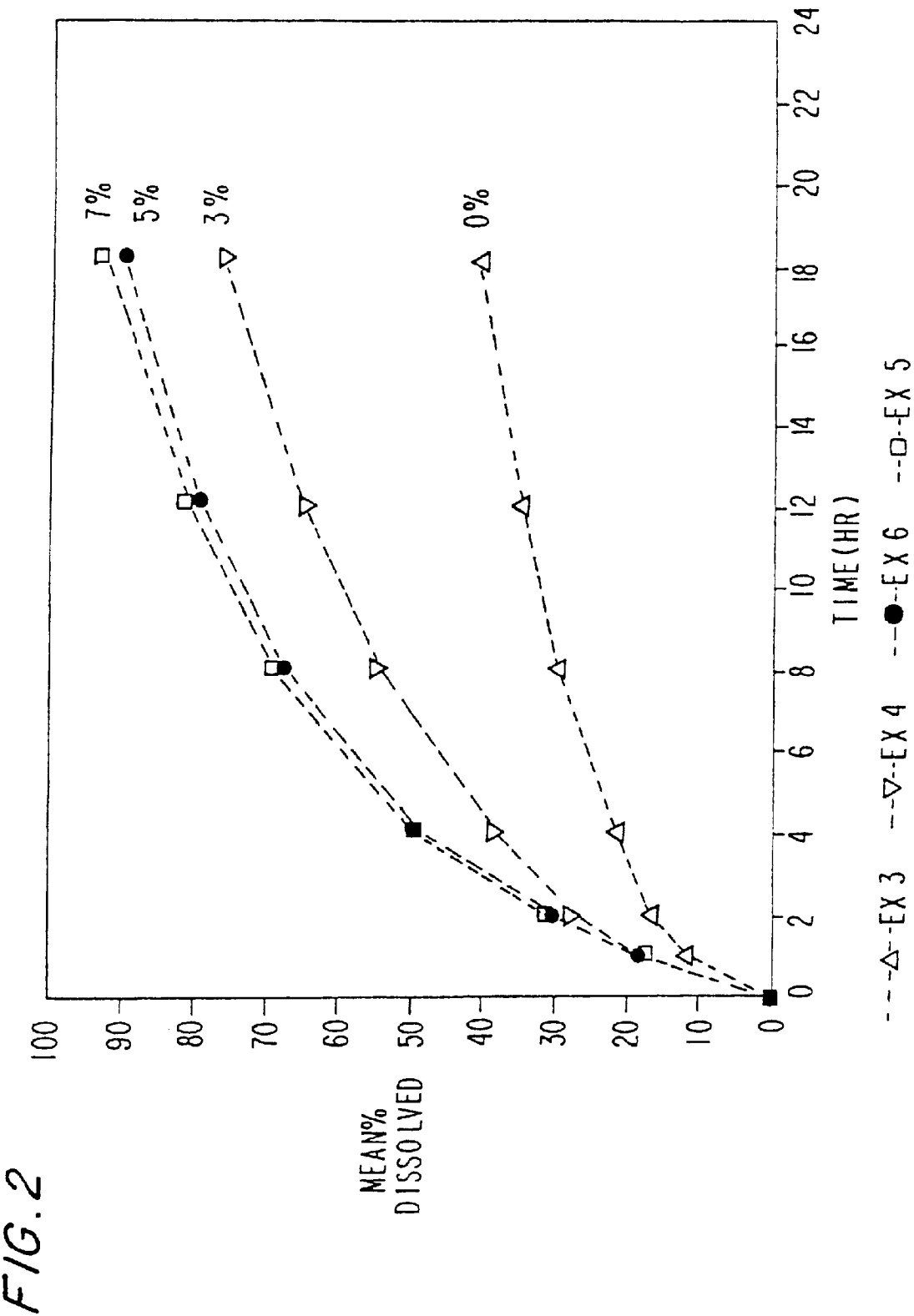
FIG. 2 is a graph displaying the dissolution rates of Example 3–6.

In one aspect of the invention, the sustained-release dosage forms comprise an opioid analgesic as the therapeutically active agent. In such formulations, the drug is incorporated into a melt-extruded strand which includes a pharmaceutically acceptable hydrophobic material such as an alkylcellulose or an acrylic polymer or copolymer. In certain embodiments, it is preferably to further add to the blend a plasticizers for the hydrophobic material in order to reduce the extrusion temperature. The choice of the most suitable plasticizer is made base don its ability to lower the glass transition temperature (Tg) of the polymer. In preferred alternative embodiments, a hydrophobic fusible carrier (which may also act as a binder) is utilized instead of a plasticizer. The hydrophobic fusible carrier preferably imparts a slower release of the therapeutically active agent form the melt extruded formulation. Any further pharmaceutical excipients known to those skilled in the art may be added as deemed necessary.

Another aspect of the invention is directed to improved melt extruded matrices which comprise a hydrophobic material and a fatty binder such as previously specified. In accordance therewith, a therapeutically active agent is combined with one or more suitable hydrophobic materials and a hydrophobic fusible carrier is extruded to form an extrudate. The extrudate may then be cut into multiparticulates which are subsequently incorporated into sustained release dosage forms.

Therapeutically Active Agents

Therapeutically active agents which may be used in accordance with the present invention include both water soluble and water insoluble drugs. Examples of such therapeutically active agents include antihistamines (e.g., dimenhydrinate, diphenhydramine, chlorpheniramine and dexchlorpheniramine maleate), analgesics (e.g., aspirin, codeine, morphine, dihydromorphone, oxycodone, et.), non-steroidal anti-inflammatory agents (e.g., naproxen, dichlofenae, indomethacin, ibuprofen, sulindac), anti-emetics (e.g., meloclopramide, methylnaltrexone), anti-epileptics (e.g., phentoin, meprobamate and nitrazepam), vasodilators (e.g., nifedipine, papaverine, diltiazem and nicardipine), anti-tussive agents and expectorants (e.g., codeine phosphate), anti-asthmatics (e.g. theophylline), antacids, anti-spasmodics (e.g. atropine, scopolamine), antidiabetics (e.g., insulin), diuretics (e.g., ethacrynic acid, bendrofluthiazide), anti-hypotensives (e.g., propranolol, clonidine), antihypertensives (e.g, clonidine, methyldopa), bronchodilators (e.g., albuterol), steroids (e.g., hydrocortisone, triamcinolone, prednisone), antibiotics (e.g., tetracycline), antihemorrhoidals, hypnotics, psychotropics, antidiarrheals, mucolytics, sedatives, decongestants, laxatives, vitamins, stimulants (including appetite suppressants such as phenylpropanolamine), as well as salts, hydrates, and solvents of the same.

In embodiments of the invention directed to opioid analgesics, the opioid analgestics used in accordance with the present invention include alfentanil, allylprodine, alphaprodine, anileridine, benzylmorphine, bezitramide, buprenorphine, butorphanol, clonitazene, codeine, cyclazocine, desomorphine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromophone, hydroxypethidine, isomethadone, ketobemidone, levallorphan, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, phopheptazine, promedol, properidine, propiram, propozyphene, sufentanil, tramadol, tilidine, salts thereof, mixtures of any of the foregoing, mixed mu-agonists/antagonists, mu-antagonist combinations, and the like. The opioid analgesic may be in the form of the free base, or in the form of a pharmaceutically acceptable salt, or in the form of a pharmaceutically acceptable complex.

In certain preferred embodiments, the opioid analgesic is selected from morphine, codeine, hydromorphone, hydrocodone, oxycodone, dihydrocodeine, dihydromorphine, oxymorphone, tramadol or mixtures thereof.

In one preferred embodiment the sustained-release opioid oral dosage form of the present invention includes hydromorphone as the therapeutically active ingredient in an amount from about 4 to about 64 mg hydromophone hydrochloride. Alternatively, the dosage form may contain molar equivalent amounts of other hydromorphone slats or of the hydromorphone base. In other preferred embodiments where the opioid analgesic is other than hydromophone, the dosage form contains an appropriate amount to provide a substantially equivalent therapeutic effect. For example, when the opioid analgesic comprises morphine, the sustained-release oral dosage forms of the present invention include from about 5 mg to about 800 mg morphine, by weight (based on morphine sulfate). When the opioid analgesic comprises oxycodone, the sustained-release oral dosage forms of the present invention include from about 5 mg to about 400 mg oxycodone. When the opioid analgesic is tramadol, the sustained-release oral dosage forms of the invention include from about 50 mg to about 800 mg tramadol by weight, based on the hydrochloride salt.

The sustained-release dosage forms of the present invention generally achieve and maintain therapeutic levels substantially without significant increases in the intensity and/or degree of concurrent side effects, such as nausea, vomiting or drowsiness, which are often associated with high blood levels of opioid analgesics. There is also evidence to suggest that the use of the present dosage forms leads to a reduced risk of drug addiction.

In the present invention, the oral opioid analgesics have been formulated to provide for an increased duration of analgesic. Surprisingly, these formulations, at comparable daily dosages of conventional immediate-release drug, are associated with a lower incidence in severity of adverse drug reactions and can also be administered at a lower daily dose than conventional oral medication while maintaining pain control.

When the therapeutically active agent included in the dosage forms of the present invention is an opioid analgesic, the dosage form may further include one or more additional which may or may not act synergistically with the opioid analgesics of the present invention. Examples of such additional therapeutically active agents include non-steroidal anti-inflammatory agents, including ibuprofen, diclofenac, naproxen, benoxaprofen, flubriprofen, fenoprofen, flubufen, ketoprofen, idoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acematacin, fentiazac, clidanac, oxpinac, mefenamic acid, meclofenamic acid, flufenamic acid, niflumic acid tolfenamic acid, diflurisal, flufenisal, piroxicam, sudoxicam or isoxicam, and the like. Other suitable additional drugs which may be included in the dosage forms of the present invention include acetaminophen, aspirin, salicylate-derived analgesics and antipyretics or salts thereof, and other non-opioid analgesics.

The additional (non-opioid) therapeutically active agent may be included in control release form or in immediate release form. The additional drug may be incorporated into the controlled release matrix along with the opioid; incorporated as a separated controlled release layer or immediate release layer; or may be incorporated as a powder, granulation, etc., in a gelatin capsule with the extrudates of the present invention.

Matrix Ingredients

The extrudates of the present invention include at lease one hydrophobic material. The hydrophobic material will preferably impart sustained release of the opioid analgesic to the final formulation. Preferred hydrophobic materials which may be used in accordance with the present invention include alkylcelluloses such as natural or synthetic celluloses derivative (e.g. ethylcellulose), acrylic and methacrylic acid polymers and copolymers, shellac, zein, was-type substances including hydrogenated castor oil or hydrogenated vegetable oil, or mixtures thereof. This list is not meant to be exclusive, and any pharmaceutically acceptable hydrophobic material which is capable of imparting sustained release of the active agent and which melts (or softens to the extent necessary to be extruded) may be used in accordance with the present invention.

In certain preferred embodiments of the present invention, the hydrophobic material is a pharmaceutically acceptable acrylic polymer, including but not limited to acrylic acid an methacrylic acid copolymers, methyl methacrylate, methyl methacrylate copolymers, ethoxyethyl methacryaltes, cynaoethyl methacrylate, aminoalkyl methacrylate copolymer, poly(acrylic acid), poly(methacrylic acid), methacrylic acid alkylamine copolymer, poly(methyl methacrylate), poly (methacrylic acid)(anhydride), polymethacrylate, polyacrylamide, poly(methacrylic acid anhydride), and glycidyl methancrylate copolymers. In other embodiments, the hydrophobic material is selected from materials such as hydroxyalkylcelluloses such as hydroxypropylmethylcellulose and mixtures of the foregoing.

The retardant material is preferably a hydrophobic fusible carrier which may comprise one or more water-insoluble wax-like thermoplastic substances possibly mixed with one or more wax-like thermoplastic substances being less hydrophobic than said one or more water-insoluble was-like substances. In order to achieve constant release, the individual was-like substances in the binder material should be substantially non-degradable and insoluble in gastrointestinal fluids during the initial release phases.

Useful water-insoluble wax-like substances may be those with a water-solubility that is lower than about 1:5,000 (w/w).

Such hydrophobic fusible carrier materials are preferably water-insoluble with more or less pronounced hydrophilic and/or hydrophobic trends. Preferably, the retardant materials useful in the invention have a melting point from about 30 to about 200° C., preferably from about 45 to about 90° C. Specifically, the hydrophobic fusible carrier may comprise natural or synthetic waxes, fatty alcohols (such as lauryl, myristyl stearyl, cetyl or preferably cetostearyl alcool), fatty acids, including but not limited to fatty acid esters, fatty acid glycerides (mono-, di-, and tri-glycerides), hydrogenated fats, hydrocarbons, normal waxes, stearic aid, stearyl alcohol and hydrophobic and hydrophilic polymers having hydrocarbon backbones. Suitable waxes include, for example, beeswax, glycowax, castor was and carnauba wax. For purposes of the present invention, a wax-like substance is defined as any material which is normally solid at room temperature and has a melting point of from about 30 to about 100° C.

Suitable hydrophobic fusible carrier materials which may be used in accordance with the present invention include digestible, lone chain ($C_8$–$C_{50}$, especially $C_{12}$–$C_{40}$), substituted or unsubstituted hydrocarbons, such as fatty acids, fatty alcohols, glyceryl esters of fatty acids, mineral and vegetable oils and natural and synthetic waxes. Hydrocarbons having a melting point of between 25° and 90° are preferred. Of the long chain hydrocarbon materials, fatty (aliphatic) alcohols are preferred in certain embodiments. The oral dosage form may contain up to 60% (by weight) of at least one digestible, long chain hydrocarbon.

In addition to the above ingredients, a sustained-release matrix may also contain suitable quantities of other materials, e.g., diluents, lubricants, binders, granulating aids, colorants, flavorants and glidants that are conventional in the pharmaceutical art. The quantities of these additional materials will be sufficient to provide the desired effect to the desired formulation. In addition to the above ingredients, a sustained-release matrix incorporating melt-extruded multiparticulates may also contain suitable quantities of other materials, e.g. diluents, lubricants, binders, granulating aids, colorants, flavorants and glidants that are conventional in the pharmaceutical art in amounts up to about 50% by weight of the particulate if desired. Specific examples of pharmaceutically acceptable carriers and excipients that may be used to formulate oral dosage forms are described in the *Handbook of Pharmaceutical Excipients*, American Pharmaceutical Association (1986), incorporated by reference herein.

In order to facilitate the preparation of a solid, sustained-release oral dosage form according to this invention there is provided, in a further aspect of the present invention, a process for the preparation of a solid, sustained-release oral dosage form according to the present invention comprising incorporating opioids or a salt thereof in a sustained-release melt-extruded matrix. Incorporation in the matrix may be effected, for example, blending the opioid analgesic, together with at least one hydrophobic material and preferably the additional retardant material (hydrophobic fusible carrier) to obtain a homogeneous mixture. The homogeneous mixture is then heated to a temperature sufficient to at least soften the mixture sufficiently to extrude the same. The resulting homogeneous mixture is then extruded, e.g., using a twin-screw extruder, to form strands. The extrudate is preferably cooled and cut into multiparticulates by any means known in the art. The strands are cooled and cut into multiparticulates. The multiparticulates are then divided into unit doses. The extrudate preferably has a diameter of from about 0.1 to about 5 mm and provides sustained release of the therapeutically active agent for a time period of from about 8 to about 24 hours.

An optional process for preparing the melt extrusion, multiparticulates and unit doses of the present invention includes directly metering into an extruder a water-insoluble retardant, a therapeutically active agent, and an optional binder; heating said homogeneous mixture; extruding said homogeneous mixture to thereby form strands; cooling said strands containing said homogeneous mixture; and cutting said strands into particles having a size form about 0.1 mm to about 12 mm; and dividing said particles into unit doses. In this aspect of the invention, a relatively continuous manufacturing procedure is realized.

The diameter of the extruder aperture or exit port can also be adjusted to vary the thickness of the extruded strands. Furthermore, the exit part of the extruder need not be round; it can be oblong, rectangular, etc. The exiting strands can be reduced to particles using a hot wire cutter, guillotine, etc.

The melt extruded multiparticulate system can be, for example, in the form of granules, spheroids or pellets depending upon the extruder exit orifice. For purposes of the present invention, the terms "melt-extruded multiparticulate (s)" and "melt-extruded multiparticulate system(s)" and "melt-extruded particles" shall refer to a plurality of units, preferably within a range of similar size and/or shape and containing one or more active agents and one or more excipients, preferably including a retardant as described herein. In this regard, the melt-extruded multiparticulates will be of a range of from about 0.1 to about 12 mm in length and have a diameter of from about 0.1 to about 5 mm. In addition, it is to be understood that the melt-extruded multiparticulates can be any geometrical shape within this size range such as beads, microspheres, seeds, pellets, etc.

A particular advantage provided by the invention is the preparation of sustained-release melt-extruded multiparticulate formulations which do not require further processing, e.g., the extrudate may simply be cut into desired lengths and divided into unit doses of the therapeutically active agent without the need of a spheronization step.

In one preferred embodiment, oral dosage forms are prepared to include an effective amount of melt-extruded multiparticulates within a capsule. For example, a plurality of the melt-extruded multiparticulates may be placed in a gelatin capsule in an amount sufficient to provide an effective sustained-release dose when ingested and contacted by gastric fluid.

In another preferred embodiment, a suitable amount of the multiparticulate extrudate is compressed into an oral tablet using conventional tableting equipment using standard techniques. Techniques and compositions for making tablets (compressed and molded), capsules (hard and soft gelatin) and pills are also described in *Remington's Pharmaceutical Sciences*, (Arthur Osol, editor), 1553–1593 (1980), incorporated by reference herein.

In yet another preferred embodiment, the extrudate can be shaped into tablets as set forth in U.S. Pat. No. 4,957,681 (Klimesch, et. al.), described in additional detail above and hereby incorporated by reference.

In yet a further embodiment, the extrudate can be shaped into suppositories containing a unit dose of the therapeutically active agent. This may be accomplished using techniques and equipment well known to those skilled in the art.

Optionally, the sustained-release melt-extruded multiparticulate system or tablets can be coated, or the gelatin capsule can be further coated, with a sustained-release coating comprising one of the hydrophobic materials described above. Such coatings preferably include a sufficient amount of hydrophobic material to obtain a weight gain level form about 2 to about 30 percent, although the overcoat may be greater depending upon the physical properties of the particular opioid analgesic compound utilized and the desired release rate, among other things. In certain preferred embodiments of the present invention, the hydrophobic polymer comprising the sustained-release coating is a pharmaceutically acceptable acrylic polymer, such as those described herein above. The solvent which is sued for the hydrophobic material in the coating may be any pharmaceutically acceptable solvent, including water, methanol, ethanol, methylene chloride and mixtures thereof.

The unit dosage forms of the present invention may further include combinations of melt-extruded multiparticulates containing one or more of the therapeutically active agents disclosed above before being encapsulated. Furthermore, the unit dosage forms can also include an amount of an immediate release therapeutically active agent for prompt therapeutic effect. The immediate release therapeutically active agent may be incorporated, e.g., as separate pellets within a gelatin capsule, or may be coated on the surface of the compressed table which has been prepared from the multiparticulate extrudate as set forth above.

The controlled-release formulations of the present invention slowly release the therapeutically active agent, e.g., when ingested and exposed to gastric fluids, and then to intestinal fluids. The controlled-release profile of the melt-extruded formulations of the invention can be altered, for example, by varying the amount of retardant, i.e., hydrophobic polymer, by varying the amount of plasticizer relative to hydrophobic polymer, by the inclusion of additional ingredients or excipients, by altering the method of manufacture, etc. In certain embodiments of the invention, the the sustained-release dosage forms of the present invention preferably release the therapeutically active agent at a rate that is independent of pH, e.g., between pH 1.6 and 7.2. In other embodiments, the formulations can be designed to provide a pH-dependent release of the therapeutically active agent.

In other embodiments of the invention, the melt extruded material is prepared without the inclusion of the therapeutically active agent, which is added thereafter to the extrudate. Such formulations typically will have the therapeutically active agent blended together with the extruded matrix material, and then the mixture would be tabletted in order to provide a slow release formulation. Such formulations may be advantageous, for example, when the therapeutically active agent included in the formulation is sensitive to temperatures needed for softening the hydrophobic material and/or the retardant material.

Opioid Analgesic Formulations

In certain preferred embodiments, the invention is directed to sustained-release oral opioid formulations which are administrable on a once-a-day basis, and which are prepared from the melt extrudates described herein. Such dosage forms will provide and in-vitro release (when assessed by the USP Paddle or Basket Method at 100 prm at 900 ml aqueous buffer (pH between 1.6 and 7.2) at 37° C. from about 1 to about 42.5% opioid released after one hour, from about 5 to about 65% opioid released after 2 hours, from about 15 to about 85% opioid released after 4 hours, from about 20 to about 90% opioid released after 6 hours, from about 35 to about 95% opioid released after 12 hours, from about 45 to about 100% opioid released after 18 hours, and from about 55 to about 100% opioid released after 24 hours, by weight. Such formulations may further be characterized by a peak plasma level at form about 2 to about 8 hours after oral administration, and preferably from about 4 to about 6 hours after administration. Such formulations are further characterized by a $W_{50}$ from about 4 to about 12 hours.

In certain preferred embodiments, the oral 24 hour sustained-release opioid dosage form provides a rapid rate of initial rinse in the plasma concentration of the opioid after oral administration, such that the peak plasma level obtained in-vivo occurs from about 2 to about 8 hours after oral administration, and/or the absorption half-life is from about 1 to about 8 hours after oral administration (in the fasted state). More preferably in this embodiment the absorption half-life is 1–6 hours and possibly 1–3 hours after oral administration (in the fasted state). Such formulations provide an in-vitro dissolution under the conditions specified above, from about 12.5 to about 42.5% opioid released after one hour, from about 25 to about 65% opioid released after 2 hours, from about 45 to about 85% opioid released after 4 hours, and greater than about 60% opioid released after 8 hours, by weight.

DETAILED DESCRIPTION OF THE PREFERRED EMBODIMENTS

The following examples illustrate various aspects of the present invention. They are not to be construed to limit the claims in any manner whatsoever.

MELT-EXTRUSION TECHNIQUES

Typical melt extrusion systems capable of carrying-out the present invention include a suitable extruder drive motor having variable speed and constant torque control, start-stop controls, and ammeter. In addition, the system will include a temperature control console which includes temperature sensors, cooling means and temperature indicators throughout the length of the extruder. In addition, the system will include an extruder such as twin-screw extruder which consists of two counter-rotating intermeshing screws enclosed within a cylinder or barrel having an aperture or die at the exit thereof. The feed materials enter through a feed hopper and is moved through the barrel by the screws and is forced through the die into strands which are thereafter conveyed such as by a continuous movable belt to allow for cooling and being directed to a pelletizer or other suitable device to render the extruded ropes into the multiparticulate system. The pelletizer can consist of rollers, fixed knife, rotating cutter and the like. Suitable instruments and systems are available from distributors such as C. W. Brabender Instruments, Inc. of South Hackensack, N.J. Other suitable apparatus will be apparent of those of ordinary skill in the art.

A further aspect of the invention is related to the preparation of melt extruded multiparticulates as set forth above in a manner which controls the amount of air included in the extruded product. By controlling the amount of air included in the extrudate, it has been surprisingly found that the release rat of the therapeutically active agent from the, e.g., multiparticulate extrudate, can be altered significantly. In certain embodiments, it has been surprisingly found that the pH dependency of the extruded product can be altered as well.

A further aspect of the invention is related to the preparation of melt extruded multiparticulates as set forth above in a manner which controls the amount of air included in the extruded product. By controlling the amount of air included in the extrudate, it has been surprisingly found that the release rate of the therapeutically active agent form the, e.g., multiparticulate extrudate, can be altered significantly. In certain embodiments, it has been surprisingly found that the pH dependency of the extruded product can be altered as well.

Thus, in a further aspect of the invention, the melt extruded product is prepared in a manner which substantially excludes air during the extrusion phase of the process. This may be accomplished, for example, by using a Leistritz extruder having a vacuum attachment. It has been surprisingly found that extruded multiparticulates prepared according to the invention using the Leistritz extruder under vacuum provides a melt-extruded product having different physical characteristics. In particular, the extrudate is substantially non-porous when magnified, e.g., using a scanning electron microscope which provides an SEM (scanning electron micrograph). Contrary to conventional thought, it has been found that such substantially non-porous formulations provide a faster release of the therapeutically active agent, relative to the same formulation prepared without vacuum. SEMs of the multiparticulates prepared using an extruder under vacuum appear very smooth, and the multiparticulates tend to be more robust than those multiparticulates prepared without vacuum. It has been observed that in at least certain formulations, the use of extrusion under vacuum provides an extruded multiparticulate product which is more pH-dependent than its counterpart formulation prepared without vacuum.

GENERAL PELLET MANUFACTURING PROCEDURE

The following technique was used to manufacture the extrudate and multiparticulates for Examples 1–26.

Blend the required amount of drug, hydrophobic material and binder along with any additional excipients.

Charge a powder feeder with proper amount of drug/excipients blend.

Set temperatures of extruder heating zones to the required temperature, depending on the formulation. Typically, the temperature should be set at about 83° C. Wait until the corresponding heat zones reach steady temperatures. Set the extruder screw rotation speed to 20 rpm. Start the feeder, the conveyor and the pelletizer. After the excipients are melted and the drug is embedded in the molten mixture, the resultant viscous mass is extruded as spaghetti-like strands. The diameter of the extruder aperture can be adjusted to vary the thickness of the resulting strand.

Set the conveyor belt speed to an appropriate speed (e.g., 3–100 ft/min). Allow the extruded semisolid strand(s) to be congealed and/or hardened while transported to the pelletizer on the conveyor belt. Additional cooling devices may be needed to ensure proper congealing. (The conveyor belt may not be needed to cool the strand, if the material conceals rapidly enough.)

Set the roller knife to an appropriate speed (e.g., to 3–100 ft/min and 100–800 rpm). Cut the congealed strands to desired size (e.g., 3–5 mm in diameter, 0.3–5 mm in length).

Collect the pellet product.

Fill a desired weight of pellets into hard gelatin capsules to obtain an appropriate doses of the drug.

DISSOLUTION METHOD

The following dissolution method was used to obtain dissolution profiles for the dosage forms of Example 1–25:

(USP 11 Paddle at 100 rpm at 37° C.)

Media—1st hour in 700 ml simulated gastric fluid (SGF), pH 1.2 without enzyme thereafter, 900 ml simulated intestinal fluid (SIF), pH 7.5 without enzyme Using HPLC procedures for assay The following examples illustrate various aspects of the present invention. They are not meant to be construed to limit the claims in any manner whatsoever.

EXAMPLES 1–2

Controlled Release Chlorpheniramine Formulations

In these examples, chlorpheniramine maleate controlled release pellets were prepared according to the above manufacturing procedure using ethylcellulose and an acrylic polymer (Eudragit RSPO), respectively as the retardant. The formulations are set forth in Tables 1 and 2 below. The dissolution of these formulations is set forth in FIG. 1. Drug release rate form ethylcellulose pellets (prepared at 105° C.) is significantly slower than that from Eudragit RSPO pellets (prepared at 85° C.).

TABLE 1

EX. 1

| Composition | Amt. (mg) per Capsule |
|---|---|
| Chlorpheniramine Maleate | 60 |
| Ethyl Cellulose | 84 |
| Stearic Acid | 36 |
| Total | 180 |

TABLE 2

EX. 2

| Composition | Amt. (mg) per Capsule |
|---|---|
| Chlorpheniramine Maleate | 60 |
| Eudragit RSPO | 84 |
| Stearic Acid | 36 |
| Total | 180 |

EXAMPLES 3–6

Controlled Release Morphine Formulations

Ex.3 The excipients used in Ex. 2 were employed to make morphine sulfate controlled release pellets.

TABLE 3

EX. 3

| Composition | Amt. (mg) per Capsule |
| --- | --- |
| Morphine Sulfate | 60 |
| Eudragit RSPO | 42 |
| Stearic Acid | 18 |
| Total | 120 |

The drug release rate of Example 3 was slower than expected especially during later hours of the dissolution.

Ex. 4–5 Examples 4–5 were prepared in accordance with Example 3 above. To increase the drug dissolution rate during later hours, varying amounts of Eudragit L-100 were incorporated in the formulation. The drug dissolution rate increases with increasing amount of Eudragit L-100 in the formulation. The morphine sulfate capsule formulation are set forth in tables 4–6 below:

TABLE 4

EX. 4

| Composition | Amt. (mg) per Capsule |
| --- | --- |
| Morphine Sulfate | 60 |
| Eudragit RSPO | 38.4 |
| Eudragit L-100 | 3.6 |
| Stearic Acid | 18 |
| Total | 120 |

TABLE 5

EX. 5

| Composition | Amt. (mg) per Capsule |
| --- | --- |
| Morphine Sulfate | 60 |
| Eudragit RSPO | 33.6 |
| Eudragit L-100 | 8.4 |
| Stearic Acid | 18 |
| Total | 120 |

Ex. 6. A sustained release morphine sulfate formulation was prepared having the ingredients listed in Table 6 below:

TABLE 6

| Ingredients | Amt(mg)/Capsule | Percentage in Formula |
| --- | --- | --- |
| Morphine Sulfate | 60 | 50 |
| Eudragit RSPO | 36 | 30 |
| Eudragit L-100 | 6 | 5 |
| Stearic Acid | 18 | 15 |
| Total | 120 | 100 |

The formulation of Example 6 was prepared as follows:

Pellet Manufacture a. Extruder system description. The twin screw extruder is consisted of a pair of counter rotating screws and a barrel block equipped with heating/cooling zones. The extrudate is delivered to a pelletizer through a conveyor belt and cut into pellets of the desirable size.

b. Manufacturing procedure-

1. Blend the drug and all the excipients in a proper mixer.
2. Place the mixture in a powder feeder.
3. Set temperatures of the extruder heating zones to approximately 83° C.
4. Set the extruder screw rotation speed to 20 rpm.
5. Start the feeder, the conveyor and the pelletizer.
6. After the excipients are melted and the drug embedded in the molten mixture, the viscous mass is extruded as spaghetti-like strands.
7. The extrudate is congealed and hardened while being delivered to the pelletizer on the conveyor belt.
8. The roller knife of the pelletizer cuts the strands into pellets of 1.5 mm in diameter and 1.5 mm in length.

Encapsulation

After the pellets were manufactured, 120 mg of pellets are encapsulated in size #2 heard gelatin capsules, rendering capsules containing 60 mg of morphine sulfate. These capsules were then tested using the following dissolution methodology:

The capsules of Examples 6 were found to have the following dissolution results:

|  | Time (hr) | | | | | | |
| --- | --- | --- | --- | --- | --- | --- | --- |
|  | 1 | 2 | 4 | 8 | 12 | 18 | 24 |
| Mean % dissolved | 16 | 33 | 52 | 72 | 84 | 95 | 102 |

Figure 3:
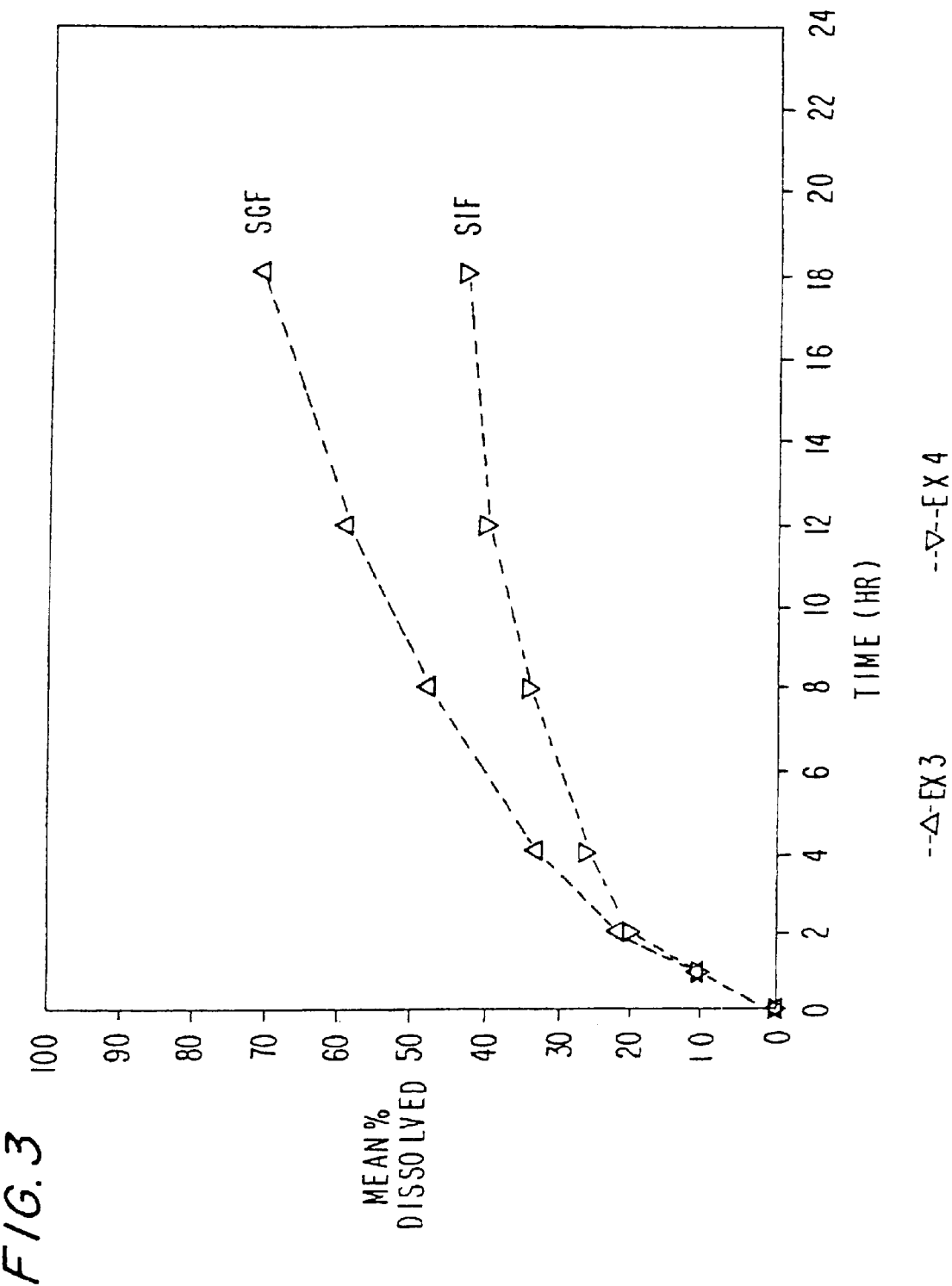
FIGS. 3 and 4 are graphs displaying the pH dependency of the dissolution results of Examples 3 and 6 respectively.

As seen in FIG. 3, the drug dissolution rate obtained from the product of Ex. 3 showed a significant pH dependency. The release rate was slower in SIF (simulated intestinal fluid) than in SGF (simulated gastric fluid).

Figure 4:
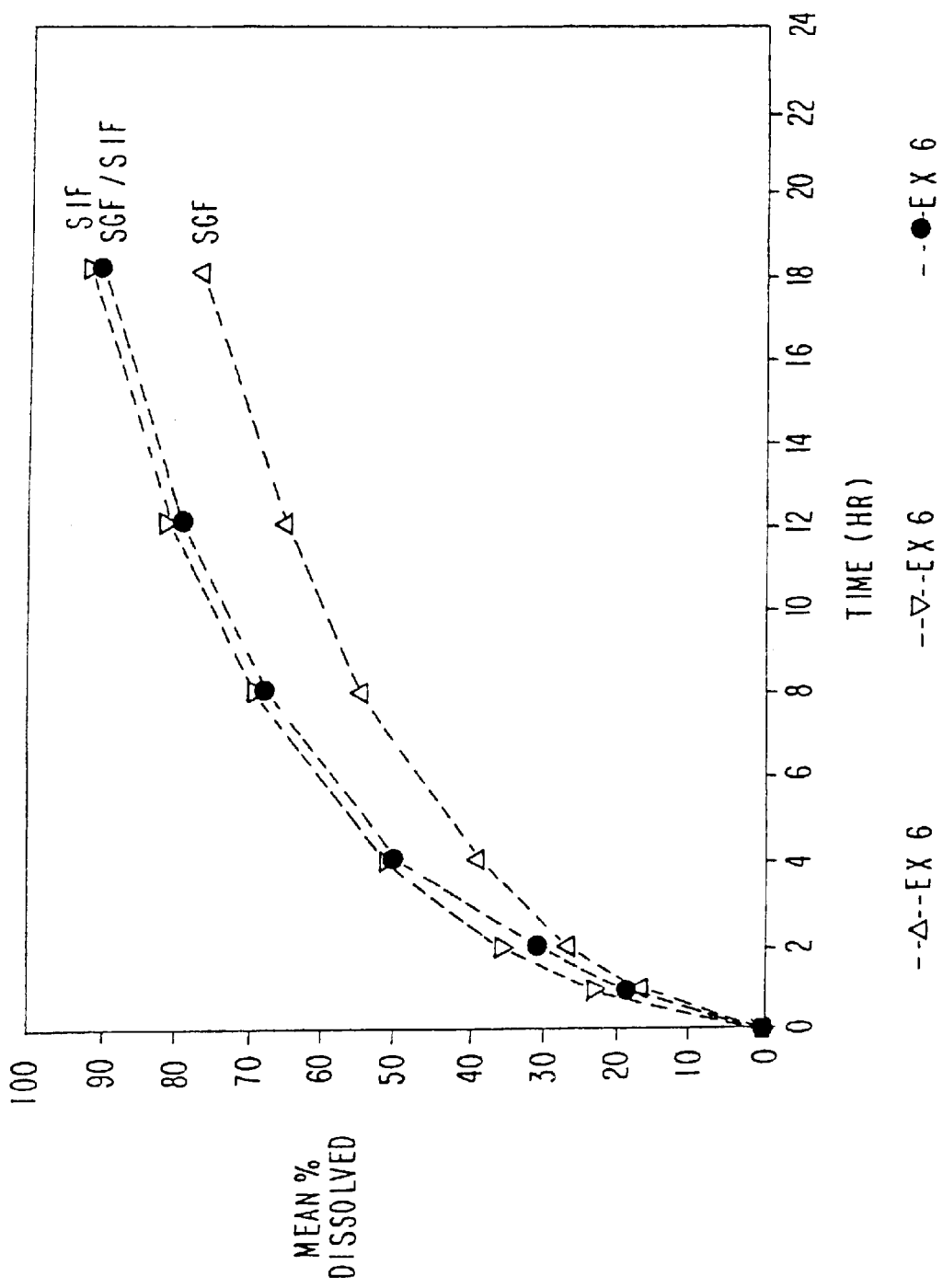

In FIG. 4, it can be seen that due to the addition of Eudragit L-100, the drug dissolution rate obtained from Ex. 6 was less pH dependent. The drug release rate was faster in SIF during later hours of dissolution which is desirable for complete bioavailablity.

EXAMPLES 7–8

Figure 5:
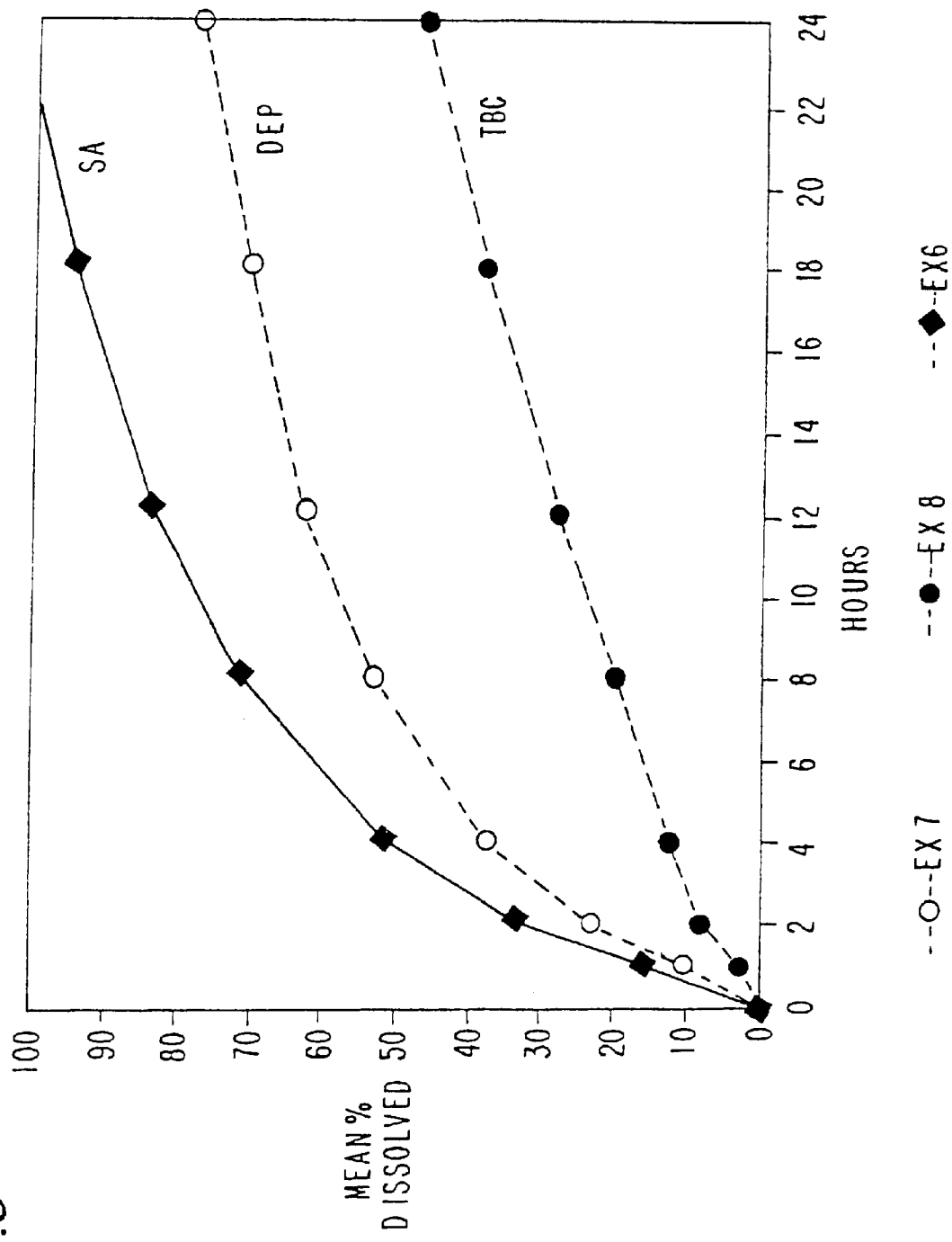
FIG. 5 is a graph displaying the dissolution results of Examples 7 and 8 vs. Example 6.

As demonstrated in FIG. 5, with proper choice of plasticizers, the drug release rate from the formula containing Eudragit L-100 can be reduced. This may be necessary to achieve desirable plasma drug concentration profiles after oral administration of the pellets.

TABLE 7

EX. 7

| Composition | Amt. (mg) per Capsule |
| --- | --- |
| Morphine Sulfate | 60 |
| Eudragit RSPO | 33.6 |
| Eudragit L-100 | 8.4 |
| Stearic Acid | 9 |
| Diethyl Phthalate | 9 |
| Total | 120 |

TABLE 8

EX. 8

| Composition | Amt. (mg) per Capsule |
| --- | --- |
| Morphine Sulfate | 60 |
| Eudragit RSPO | 33.6 |
| Eudragit L-100 | 8.4 |
| Stearic Acid | 9 |
| Tributyl Citrate | 9 |
| Total | 120 |

EXAMPLES 9–10

Figure 6:
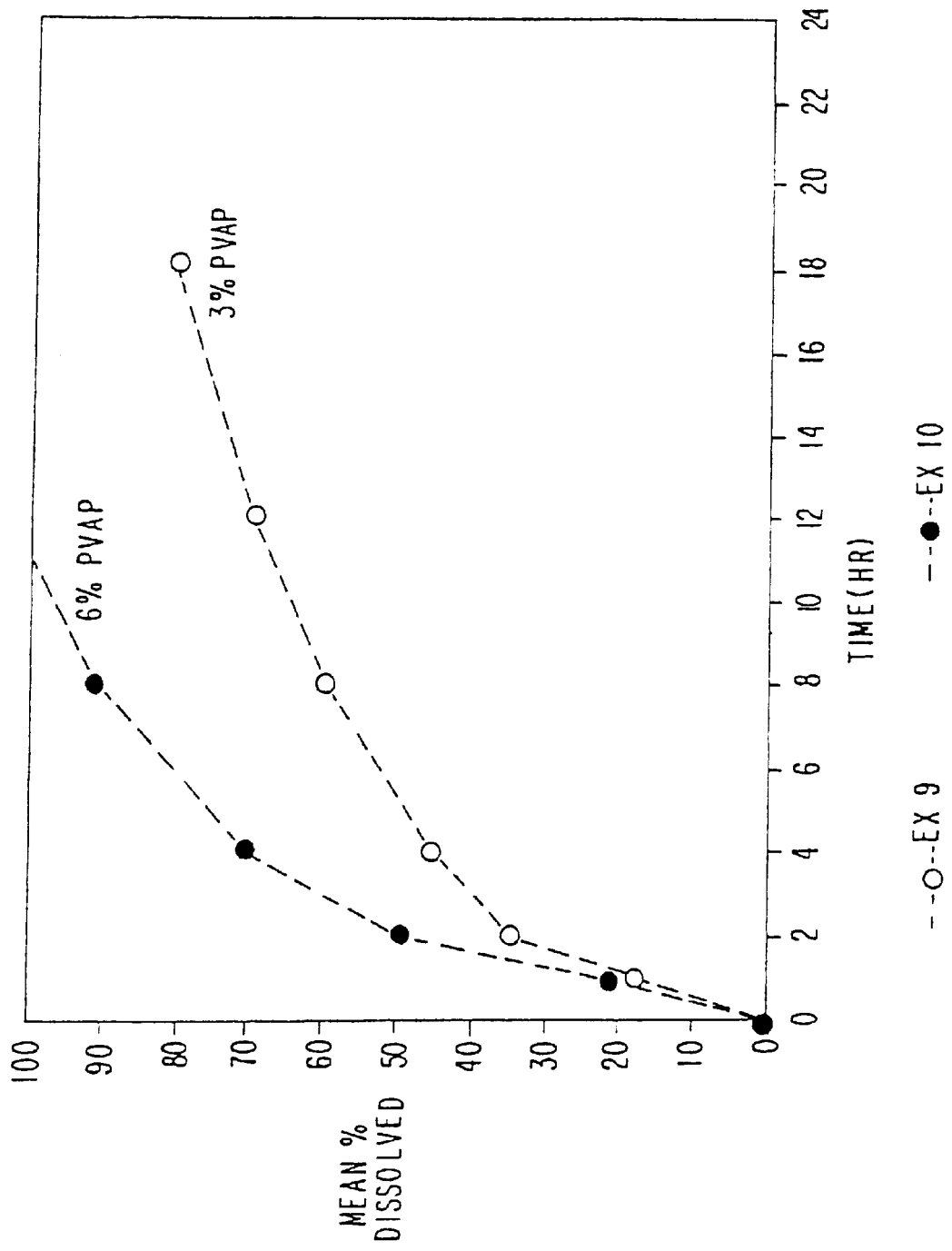
FIG. 6 is a graph displaying the dissolution results of Examples 9 and 10.

A different polymer/wax combination was used as a alternative formulation. As seen in FIG. 6, the drug dissolution rate from ethylcellulose/polyvinyl acetate phthalate was somewhat faster.

TABLE 9

EX. 9

| Composition | Amt. (mg) per Capsule |
| --- | --- |
| Morphine Sulfate | 60 |
| Ethyl Cellulose | 38.4 |
| Polyvinyl Acetate Phthalate | 3.6 |
| Stearic Acid | 18 |
| Total | 120 |

TABLE 10

EX. 10

| Composition | Amt. (mg) per Capsule |
| --- | --- |
| Morphine Sulfate | 60 |
| Ethyl Cellulose | 34.8 |
| Polyvinyl Acetate Phthalate | 7.2 |
| Stearic Acid | 18 |
| Total | 120 |

EXAMPLES 11–14

Controlled Release Oxycodone Formulations

Figure 7:
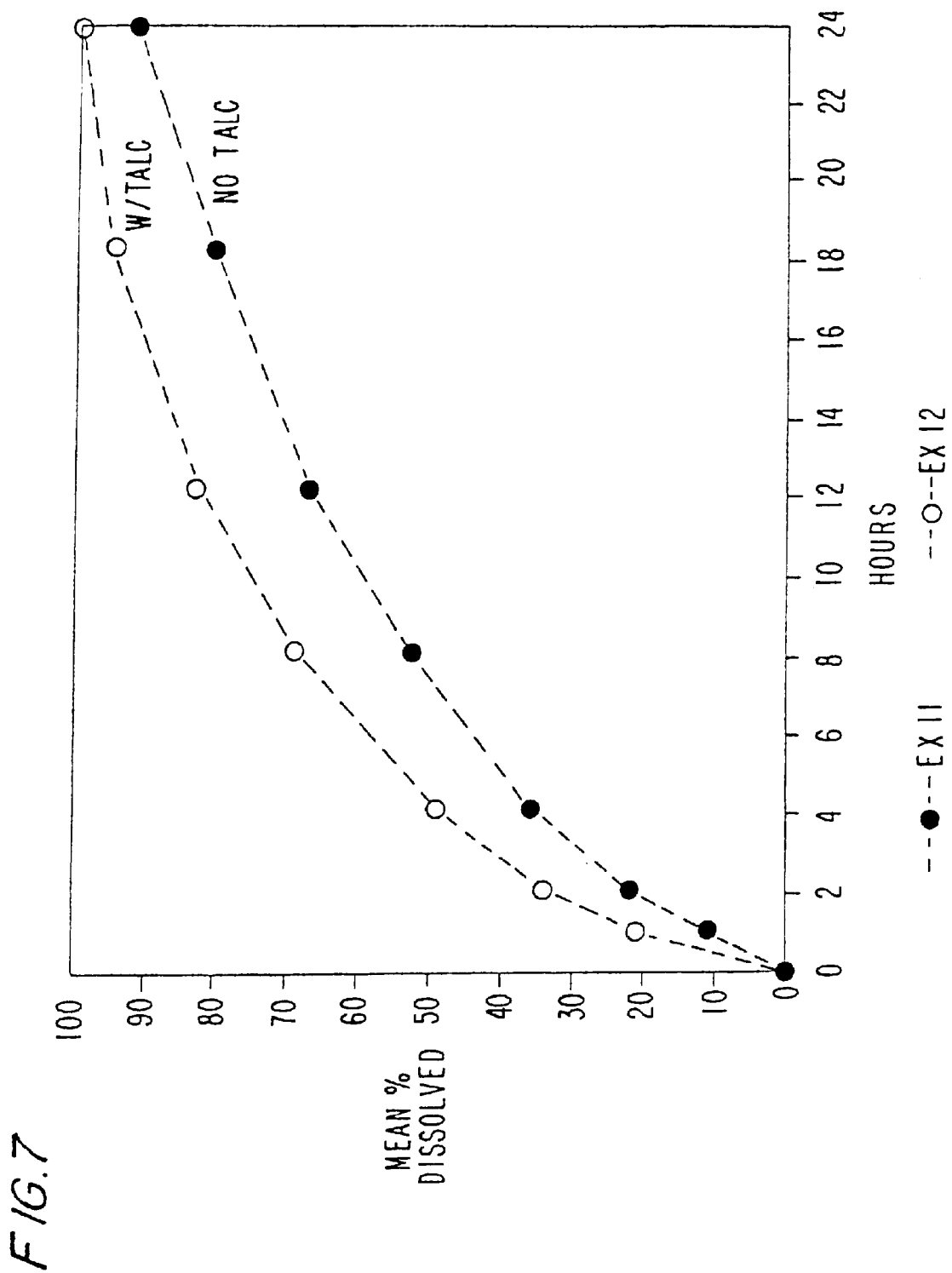
FIG. 7 is a graph displaying the dissolution results of Examples 11 and 12.

The formula used in Ex. 6 was applied to oxycodone hydrochloride. Due to the higher potency of oxycodone, only 20 mg of drug was used. The missing 40 mg was replaced by 40 mg of talc (Ex. 12). No replacement was used in Ex. 11. When tested in only SGF or SIF, the use of Eudragit L causes the formulation to become less pH dependent. The results are shown in FIG. 7.

TABLE 11

| Ingredients | Amt(mg)/Capsule | Percentage in Formula |
| --- | --- | --- |
| Oxycodone HCL | 20 | 25 |
| Eudragit RSPO | 36 | 45 |
| Eudragit L-100 | 6 | 7.5 |
| Stearic Acid | 18 | 22.5 |
| Total | 80 | 100 |

The pellet manufacturing procedure and the dissolution method are the same as described in Example 6.

The above capsules were found to have the dissolution results set forth in Table 11a below:

TABLE 11a

| | Time (hr) | | | | | | |
| --- | --- | --- | --- | --- | --- | --- | --- |
| | 1 | 2 | 4 | 8 | 12 | 18 | 24 |
| Mean % dissolved | 14 | 29 | 45 | 66 | 81 | 94 | 101 |

TABLE 12

EX. 12

| Composition | Amt. (mg) per Capsule |
| --- | --- |
| Oxycodone Hydrochloride | 20 |
| Eudragit RSPO | 36 |
| Eudragit L-100 | 6 |
| Stearic Acid | 18 |
| Talc | 40 |
| Total | 120 |

Ex. 13 Oxycodone HCl once-a-day capsules were produced with the following formula using the technology described in Example 6. The formulation is set forth in Table 13 below.

TABLE 13

| Ingredients | Amt(mg)/Capsule | Percentage in Formula |
| --- | --- | --- |
| Oxycodone HCl | 20 | 25 |
| Eudragit RSPO | 39 | 48.75 |
| Eudragit L-100 | 3 | 3.75 |
| Stearic Acid | 18 | 22.5 |
| Total | 80 | 100 |

The pellet manufacturing procedure is the same as described in Example 6. However, 80 mg of pellets were encapsulated to contain 20 mg of oxycodone HCL.

The above capsules were tested using the following dissolution methodology:

1. Apparatus—USP type II (paddle), 100 rpm at 37° C.

2. Media—Either 900 ml simulated gastric fluid (SGF), pH 1.2 without enzyme; or 900 ml simulated intestinal fluid (SIF), pH 7.5 without enzyme.

3. Analytical method—High performance liquid chromatography.

The dissolution results are set forth in Table 13a below:

TABLE 13a

| | Time (hr) | | | | | | |
| --- | --- | --- | --- | --- | --- | --- | --- |
| | 1 | 2 | 4 | 8 | 12 | 18 | 24 |
| Mean % dissolved (SGF) | 13 | 20 | 29 | 41 | 51 | 62 | 71 |
| Mean % dissolved (SIF) | 14 | 21 | 31 | 44 | 57 | 68 | 80 |

Ex. 14 To prepare an oxycodone HCl controlled release tablet which would dissolve preferentially in a lower pH, the following formula is used:

TABLE 14

| Ingredients | Amt(mg)/Tablet | Percentage in Formula |
|---|---|---|
| Oxycodone HCl | 40 | 30.8 |
| Eudragit RS30D (solid) | 14 | 10.8 |
| Spray Dried Lactose | 35.25 | 27.1 |
| PVP | 5 | 3.9 |
| Triacetin | 2 | 1.5 |
| Stearyl Alcohol | 25 | 19.2 |
| Talc | 2.5 | 1.9 |
| Magnesium Stearate | 1.25 | 0.9 |
| Film Coat | 5 | 3.9 |
| Total | 130 | 100 |

Total Manufacture

1. Mix Eudragit RS30D (suspension) and Triacetin for 5 minutes.
2. Place spray dried lactose, oxycodone HCl, PVP, in a fluid bed drier.
3. Spray the suspension onto the powders under fluidization.
4. Pass the granulation though a Comil to reduce lumps.
5. Melt stearyl alcohol at 70° C.
6. Incorporate the molten stearyl alcohol into the dry granulation in a Collete Mixer.
7. Transfer the waxed granulation to a cooling tray and allow the granulation to congeal.
8. Pass the granulation through a Comil.
9. Mix the waxed granulation with talc and magnesium stearate in a Collete Mixer.
10. Compress the lubricated granulation into tablets using a rotary tablet press.
11. Film coat the tablets.

These tablets were then tested using the following dissolution methodology described in Example 13.

The above tablets were found to have the following dissolution results:

TABLE 14a

| | Time (hr) | | | | |
|---|---|---|---|---|---|
| | 1 | 2 | 4 | 8 | 12 |
| Mean % dissolved SGF | 39 | 53 | 70 | 90 | 99 |
| Mean % dissolved SIF | 35 | 48 | 65 | 83 | 93 |

EXAMPLES 15–19

Controlled Release Hydromorphone Formulations

Figure 8:
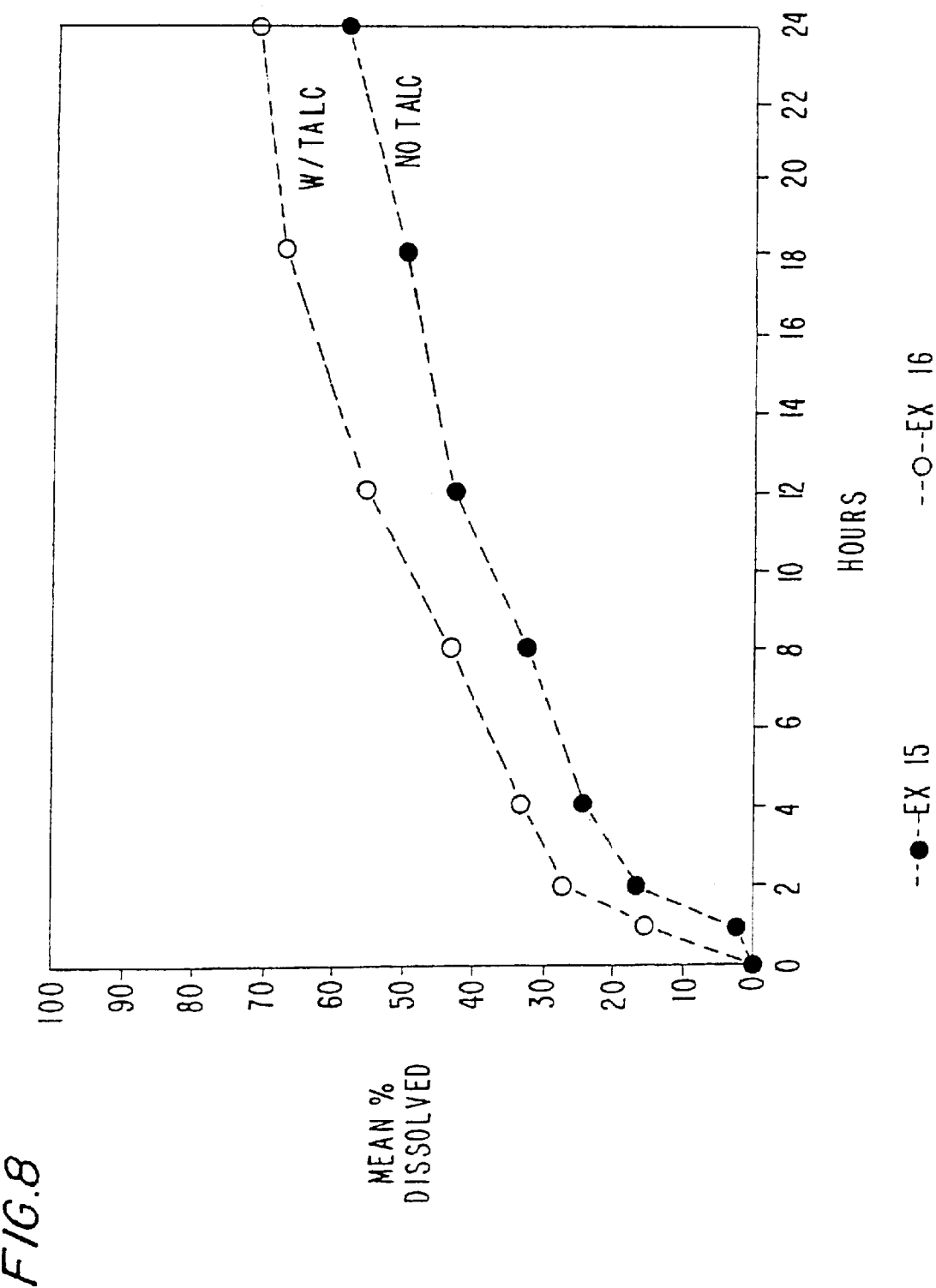
FIG. 8 is a graph displaying the dissolution results of Examples 15 and 16.
Figure 9:
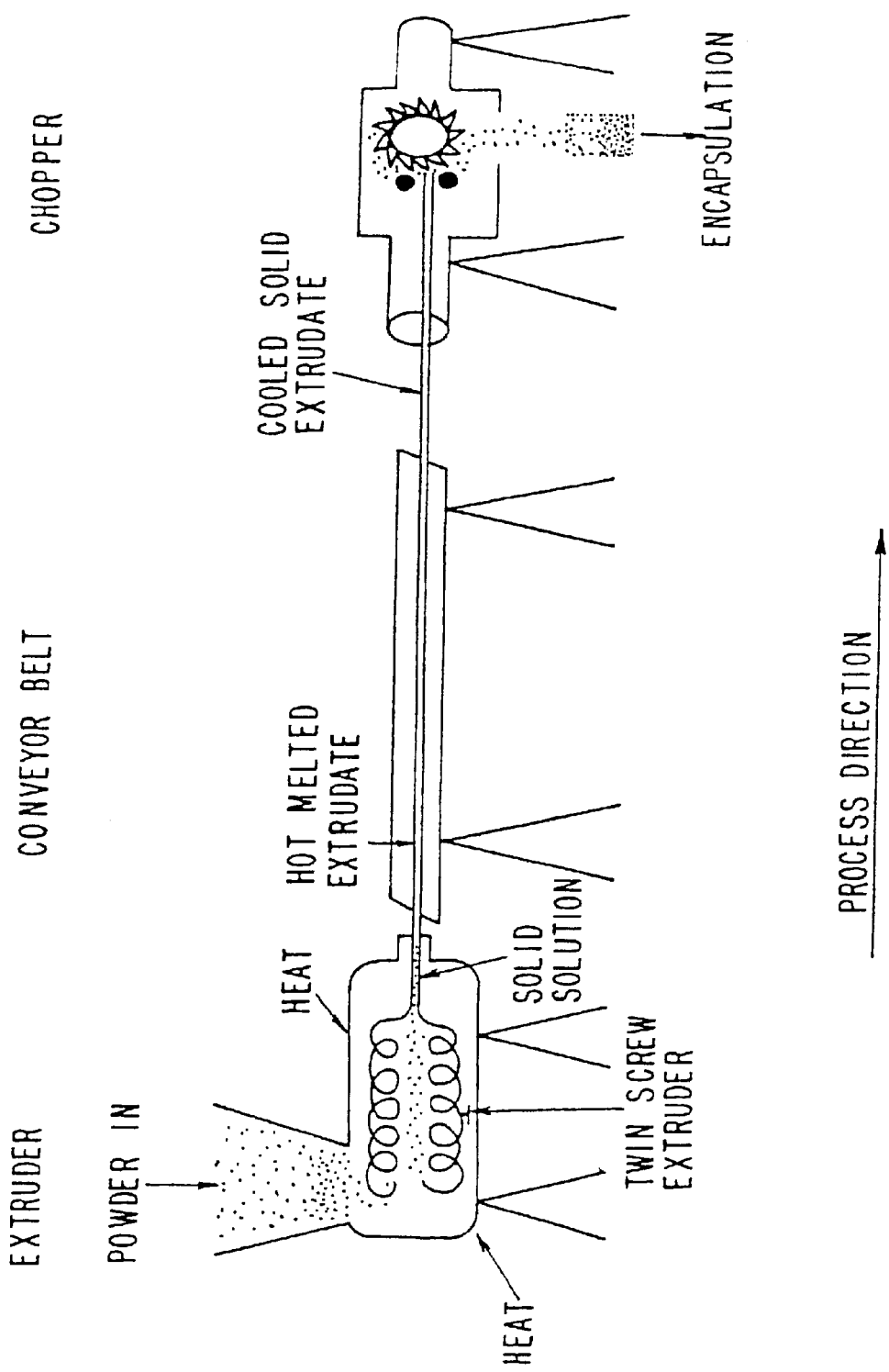
FIG. 9 is a schematic representation of a system for carrying out the present invention.

Ex. 15–16 The formula used in Ex. 6 was applied to hydromorphone hydrochloride. Due to the higher potency of hydromorphone, only 8 mg of drug was used. The missing 52 mg was replaced by 52 mg of talc (Ex. 16) or 52 mg of excipients (Ex. 15). The results are shown in FIG. 8.

TABLE 15

EX. 15

| Composition | Amt. (mg) per Capsule |
|---|---|
| Hydromorphone Hydrochloride | 8 |
| Eudragit RSPO | 67.2 |
| Eudragit L-100 | 11.2 |
| Stearic Acid | 33.6 |
| Total | 120 |

TABLE 16

EX. 16

| Composition | Amt. (mg) per Capsule |
|---|---|
| Hydromorphone Hydrochloride | 8 |
| Eudragit RSPO | 36 |
| Eudragit L-100 | 6 |
| Stearic Acid | 18 |
| Talc | 52 |
| Total | 120 |

Ex. 17 Hydromorphone HCl once-a-day capsules were produced with the formula set forth in Table 17 below using the technology described in Example 6.

TABLE 17

| Ingredients | Amt(mg)/Capsule | Percentage in Formula |
|---|---|---|
| Hydromorphone HCL | 8 | 10 |
| Eudragit RSPO | 53 | 66.25 |
| Stearyl Alcohol | 19 | 23.75 |
| Total | 80 | 100 |

The pellet manufacturing procedure is the same as describe din Example 6. However, pellets of 1.0 mm in diameter and 1.0 mm in length were prepared. Each capsule holds 80 mg of pellets and contains 8 mg of hydromorphone HCL.

The above capsules were tested using the dissolution methodology described in Example 6.

The above capsules were found to have the dissolution results set forth in Table 17a below:

TABLE 17a

| | Time (hr) | | | | | | |
|---|---|---|---|---|---|---|---|
| | 1 | 2 | 4 | 8 | 12 | 18 | 24 |
| Mean % dissolved | 17 | 28 | 32 | 45 | 56 | 69 | 82 |

Ex. 18 Hydromophone HCl once-a-day capsules were produced with the formula set forth in Table 18 below as the second example of the technology described in Example 6.

TABLE 18

| Ingredients | Amt(mg)/Capsule | Percentage in Formula |
|---|---|---|
| Hydromorphone HCl | 8 | 10 |
| Eudragit RSPO | 48 | 60 |
| Stearyl Alcohol | 24 | 30 |
| Total | 80 | 100 |

The pellet manufacturing procedure and the dissolution method are the same as described in Example 6.

The above capsules were found to have the dissolution results set forth in Table 18a below:

TABLE 18a

| | Time (hr) | | | | | | |
|---|---|---|---|---|---|---|---|
| | 1 | 2 | 4 | 8 | 12 | 18 | 24 |
| Mean % dissolved | 23 | 29 | 40 | 56 | 69 | 84 | 96 |

Ex. 19 Hydromorphone HCl once-a-day capsules were produced with the following formula according to the method described Example 6.

TABLE 19

| Ingredients | Amt(mg)/Capsule | Percentage in Formula |
|---|---|---|
| Hydromorphone HCL | 8 | 10 |
| Eudragit RSPO | 41.5 | 51.9 |
| Eudragit L-100 | 8.5 | 10.6 |
| Stearic Acid | 22 | 27.5 |
| Total | 80 | 100 |

The manufacturing procedure of the pellets and the dissolution method are the same as described in Example 6.

The above capsules were found to have the following dissolution results:

TABLE 19a

| | Time (hr) | | | | | | |
|---|---|---|---|---|---|---|---|
| | 1 | 2 | 4 | 8 | 12 | 18 | 24 |
| Mean % dissolved | 4 | 14 | 36 | 52 | 64 | 75 | 84 |

EXAMPLE 20

Figure 10:
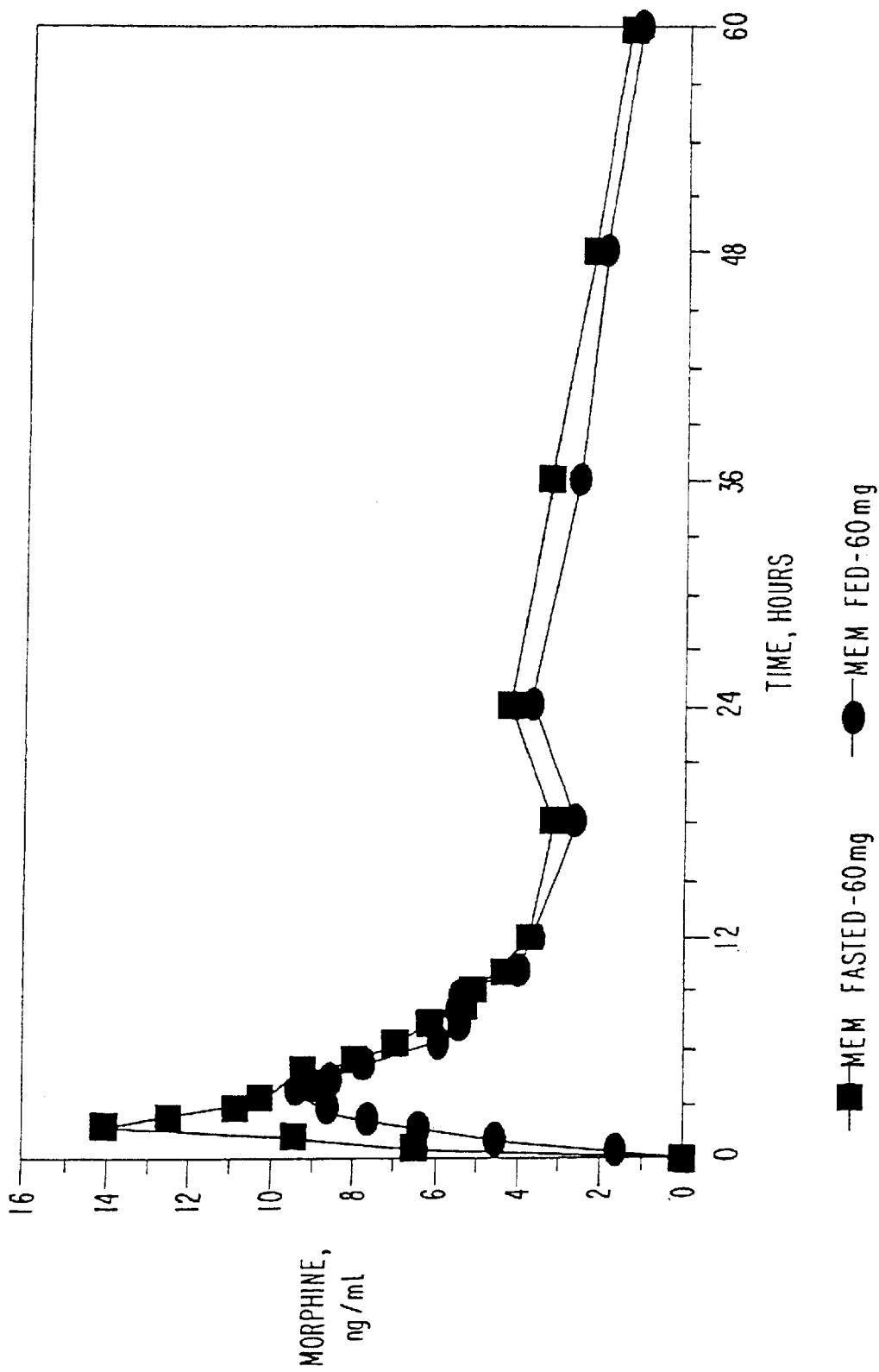
FIG. 10 is a graph displaying the fed/fast bioavailablity results for Example 20.

In this Example, a bioavailablity study was undertaken. Fourteen subjects were given the morphine sulfate formulations of Example 3. The results are provided in Table 20 below in FIG. 10.

TABLE 20

| Group | AUC | Cmax | Tmax |
|---|---|---|---|
| Example 3 Fasted | 230 | 15.7 | 2.1 |
| Example 3 Fed | 213 | 14.0 | 3.2 |

From the above data, it can be seen that the formulation is an ideal candidate for an extended release or once-a-day product without a food effect.

EXAMPLE 21

Bioavailablity of Morphine Sulfate Melt Extrusion Multiparticulate 60 mg Capsules A bioavailablity study of morphine capsules of Example 6 was conducted in 12 normal male volunteers. Capsules of 60 mg in strength were administered either with or without food in a single dose, two-way crossover study. Blood samples were taken periodically and assayed for morphine concentrations using gas chromatography with mass detection (G/MS). From the data, the following pharmacokinetic parameters were calculated and are indicated in Table 21 below.

TABLE 21

| Treatment | AUC, n · hr/ml | Cmax, n/ml | Tmax, hr |
|---|---|---|---|
| Fasted | 228 | 15.7 | 2.1 |
| Fed | 210 | 14.0 | 3.2 |

Figure 11:
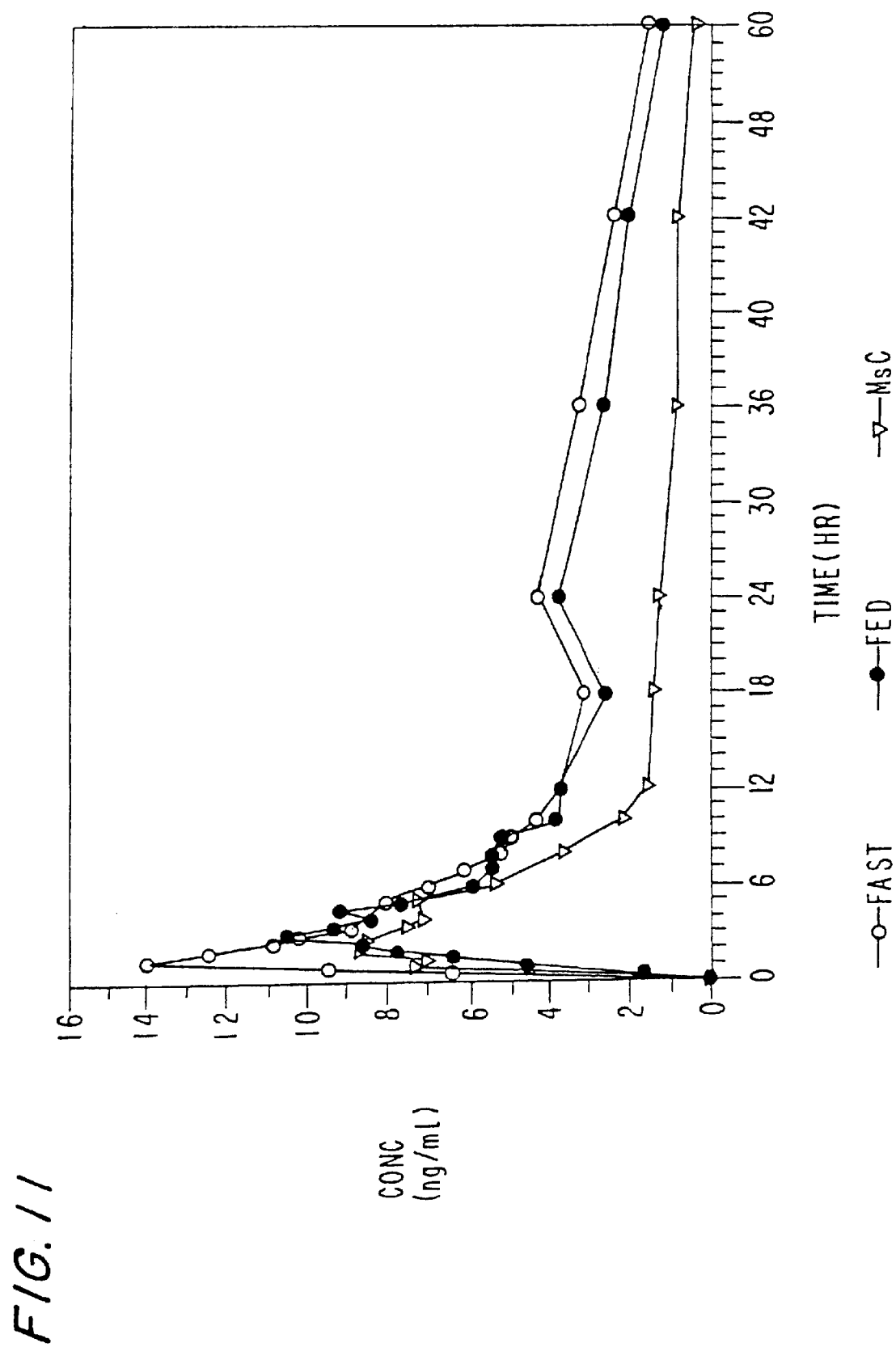
FIG. 11 is a graph displaying the plasma morphine concentrations of Example 21 obtained form administration of the capsules from Example 6 vs. MS Conti®.

When compared to the typical blood levels of MS Contin®, a single dose twice-a-day marketed morphine sulfate 30 mg tablets, in the fasted state, it can be seen that the capsules of Example 6 are suitable for once daily administration. At the 24th hour the blood levels are well above MS-Contin and within the therapeutic range (FIG. 11).

EXAMPLE 22

Bioavailablity of OXY-MEM 20 mg Capsules.

A bioavailablity sturdy of oxycodone capsules of examples 11 and 13 was conducted in 10 normal male volunteers. Capsules of example 13 were administered either with or without food. Capsules of example 11 were administered without food. The study was conducted in a single dose, four-way crossover design. Blood samples were taken periodically and assayed for oxycodone concentrations using gas chromatography with mass detection (G/MS).

From the data, the following pharmacokinetic parameters were calculated as set forth in Table 22 below:

TABLE 22

| Treatment | AUC, n · hr/ml | Cmax, n/ml | Tmax, hr |
|---|---|---|---|
| Example 13, fasted | 207 | 9.7 | 5.3 |
| Example 13, fed | 261 | 14.8 | 6.4 |
| Example 11, fasted | 244 | 12.9 | 6.0 |
| Oxycontin, fasted | 249 | 20.8 | 3.2 |

Figure 12:
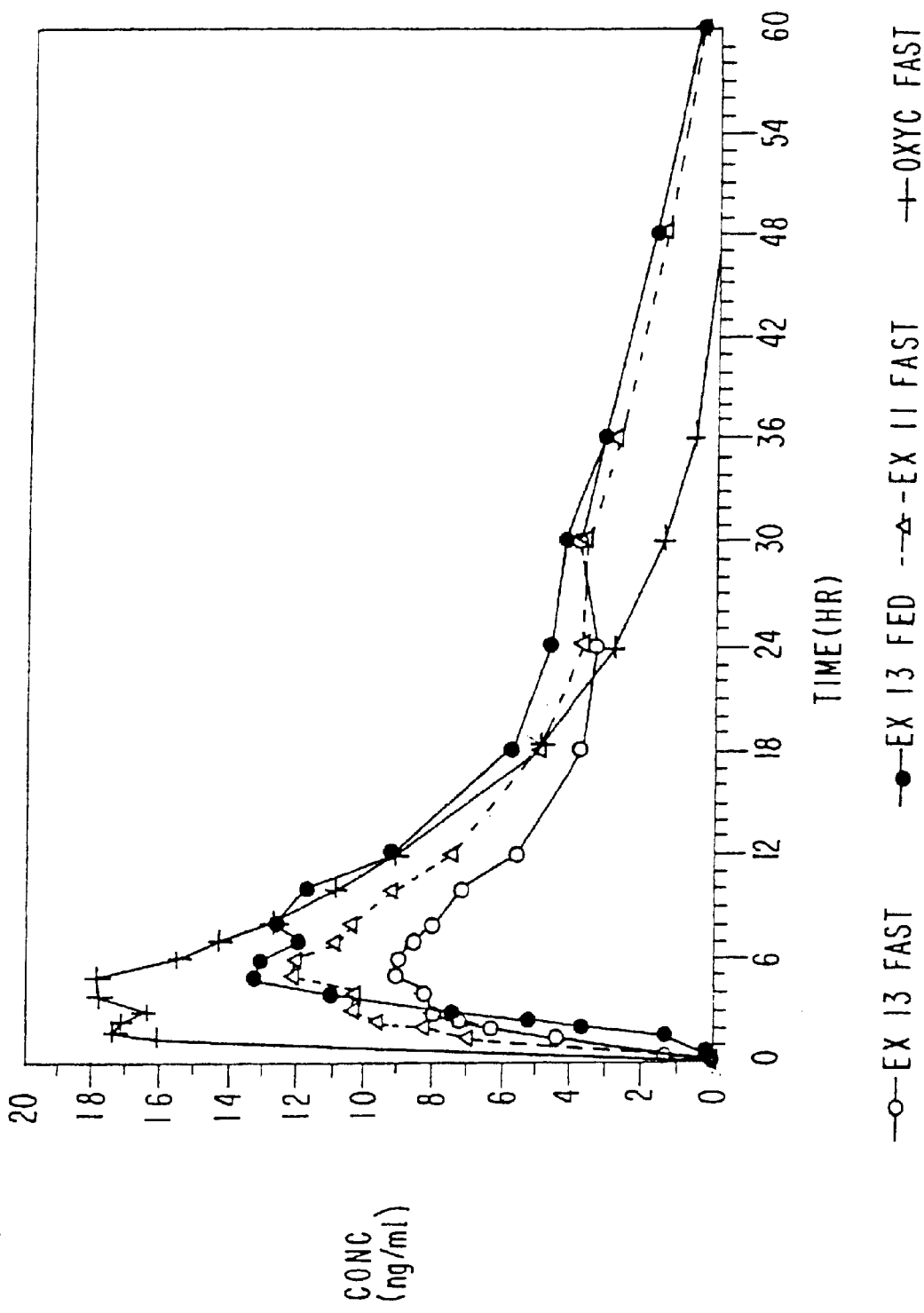
FIG. 12 is a graph displaying the plasma oxycodone concentrations of Example 22 obtained from administrating the capsules from Example 11 and 13 vs. OxyContin®.

From the above data, it can be concluded that both Examples 11 and 13, but particularly Example 13, are suitable for once daily administration. This is shown graphically in FIG. 12.

EXAMPLE 23

Bioavailablity of Example 14 Tablets

Figure 13:
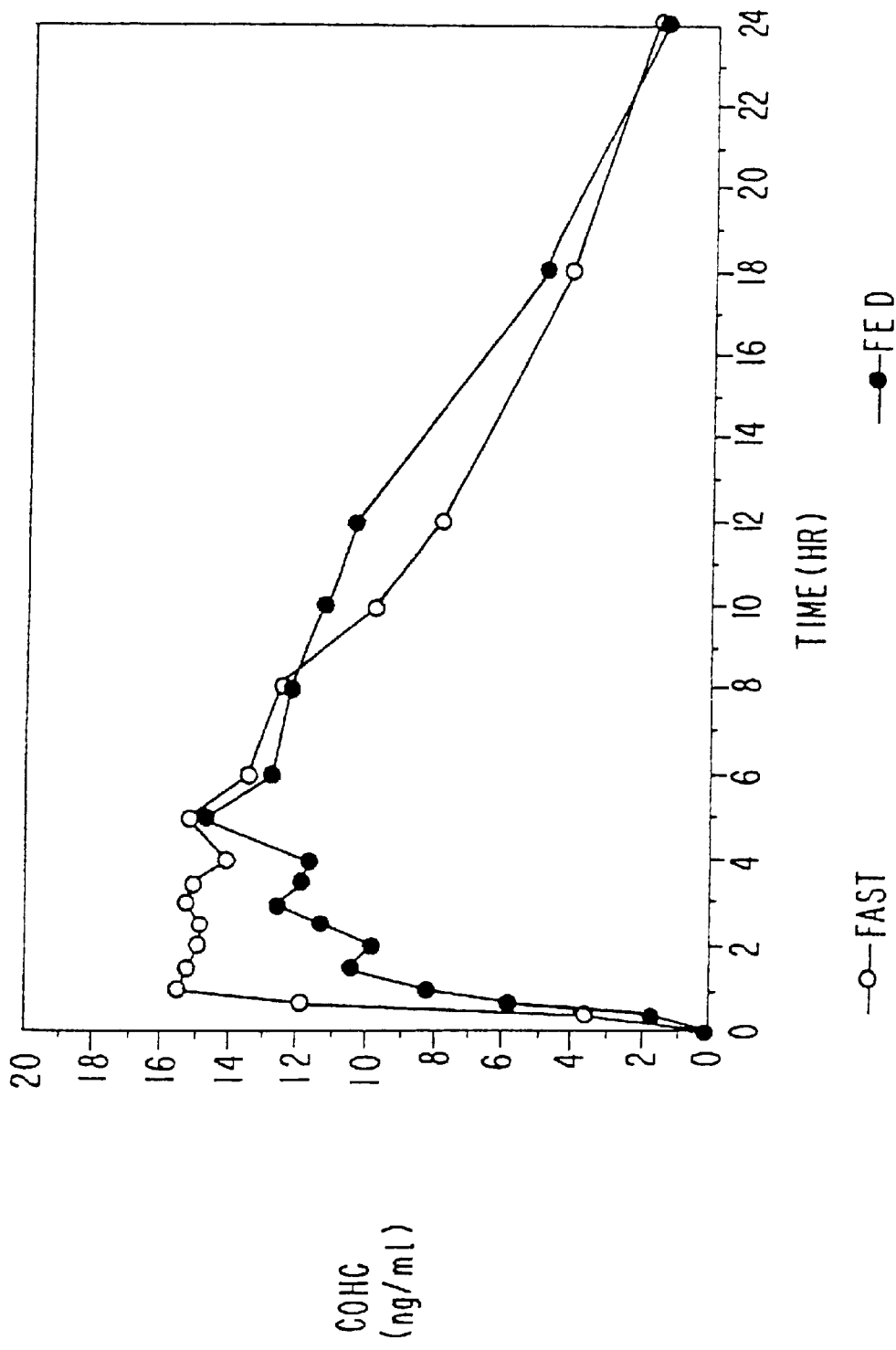
FIG. 13 is a graphical representation of the plasma oxycodone concentrations of Example 14.

A bioabailability study of oxycodone controlled release tablets of example 14 was conducted in 25 normal volunteers. These tablets were administered either with or without food. The study was conducted in a single dose, randomized crossover design. Blood samples were taken periodically and assayed for oxycodone concentrations using gas chromatography with mass detection (GC/MS). The plasma oxycodone concentration versus time curves are shown in FIG. 13.

From the data, the following pharmacokinetic parameters were calculated.

TABLE 23

| Treatment | AUC, ng · hr/ml | Cmax, ng/ml | Tmax, hr |
| --- | --- | --- | --- |
| Example 14, fasted | 422 | 39.3 | 3.1 |
| Example 14, fed | 416 | 35.3 | 4.8 |

Surprisingly, it was found that the controlled release oxycodone HCl preparation, which dissolved preferentially in low pH, does not show substantial food effect. From the Cmax data, it can be seen that there is no significant change in blood oxycodone levels when the drug was taken with food than without food (35.3/39.3=0.09). From the AUC (area under the curve) data, it appears that the amount of drug absorbed with or without food is similar (416/422= 0.986).

EXAMPLE 24

Bioavailablity of HH-MEM 8 mg Capsules

A bioavailablity study of hydromorphone capsules of Examples 17 and 18 was conducted using a single dose, five-way crossover study in 12 normal male volunteers. The subjects received either 8 mg of Dilaudid tablet (immediate release) or 8 mg of HH-MEM capsules. Dilaudid tablets were administered after an overnight fast. MEM capsules were administered with or without food. Blood samples were taken periodically and assayed for hydromorphone concentrations using gas chromatography with mass detection (G/MS). From the data, the following pharmacokinetic parameters were calculated.

TABLE 24

| Treatment | AUC, n · hr/ml | Cmax, n/ml | Tmax, hr |
| --- | --- | --- | --- |
| Example 17, fasted | 19.00 | 0.72 | 6.8 |
| Example 17, fed | 20.10 | 0.75 | 2.4 |
| Example 18, fasted | 19.23 | 0.76 | 3.9 |
| Example 18, fed | 21.47 | 0.93 | 1.9 |
| Dilaudid, fasted | 14.55 | 3.69 | 0.7 |

Figure 14:
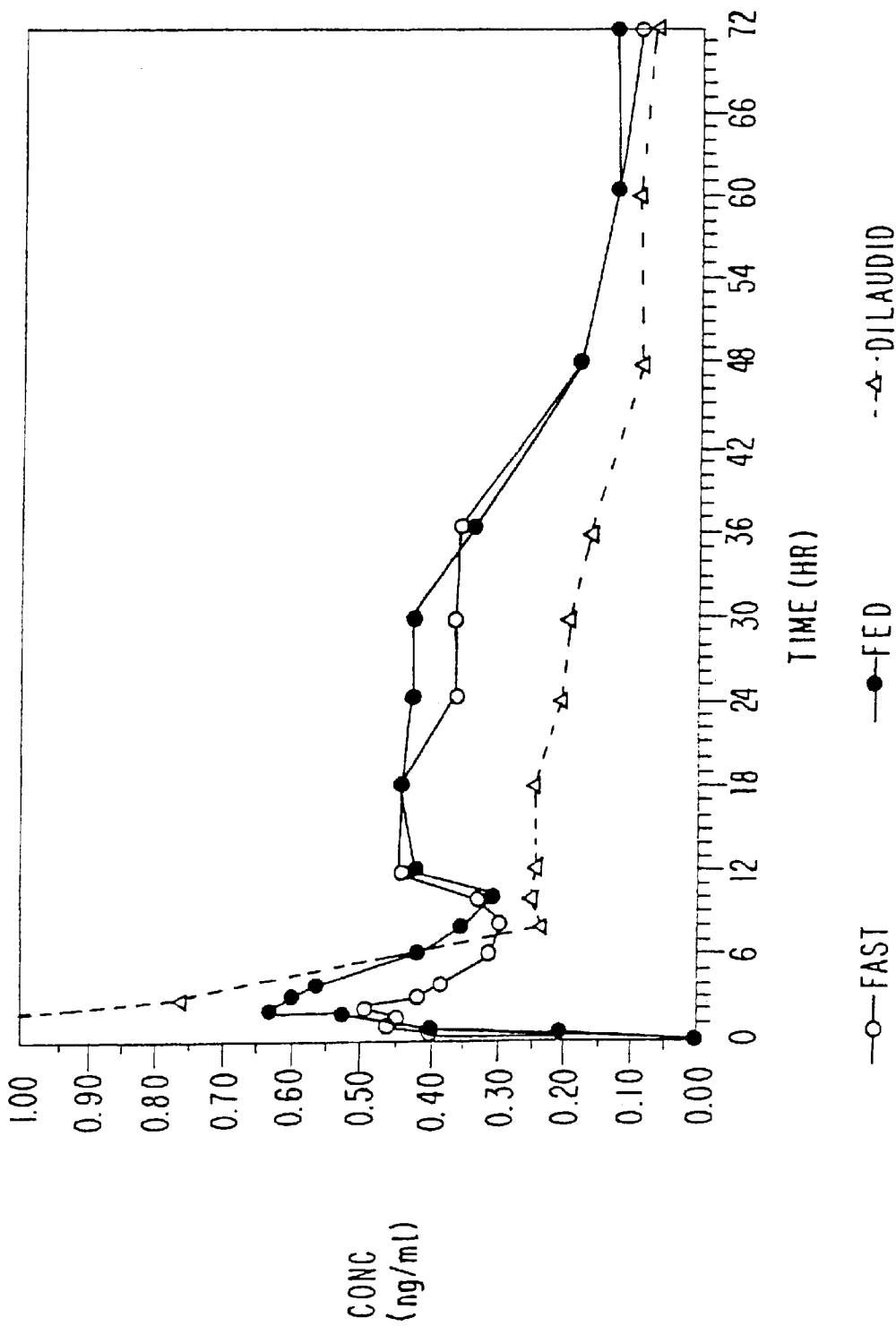
FIG. 14 is a graphical representation of the hydromorphone concentrations of Example 24 using the capsules from example 17 vs. Dilaudid®.
Figure 15:
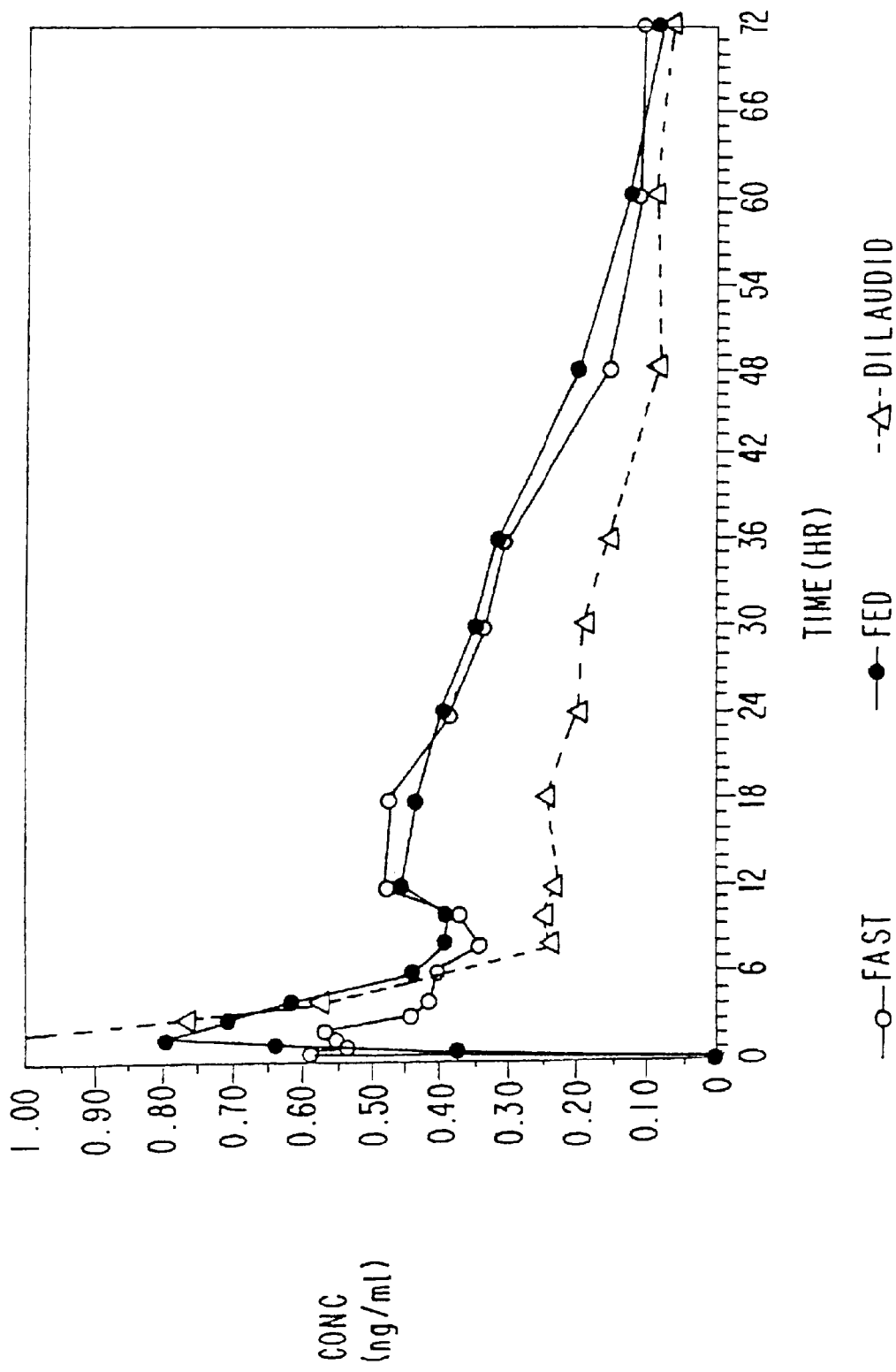
FIG. 15 is a graph displaying the plasma hydromorphone concentrations of Example 24 using the capsules of Example 18 vs. Dilaudid®.

From the data, both formulations 17 and 18 would be suitable for once-a-day administration both not having a food effect, and in fact Example 17 looks ideal. The data of Example 17 is shown graphically in FIG. 14 and the data of Example 18 is shown graphically in FIG. 15.

EXAMPLE 25

Steady State Bioavailablity of HH-MEM 8 mg Capsules

To assess steady state plasma levels and the effect of food on hydromorphone, a single dose, two-way crossover study was conducted in 12 normal male volunteers. The subjects received either 4 mg of Dilaudid (immediate release) every 6 hours or 16 mg of the capsules according to Example 17 every 24 hours. Venous blood samples were taken at predetermined time points. The plasma hydromorphone concentrations were quantitated using gas chromatography with mass detection (G/MS).

From the data from day 4, the following pharmacokinetic parameters were calculated and are set forth in Table 25 below.

TABLE 25

| Treatment | AUC, n · hr/ml | Cmax, n/ml | Cmin, n/ml | Tmax, hr |
| --- | --- | --- | --- | --- |
| Example 17 | 36.08 | 2.15 | 1.49 | 5.8 |
| Dilaudid | 33.53 | 3.44 | 0.94 | 1.6 |

Figure 16:
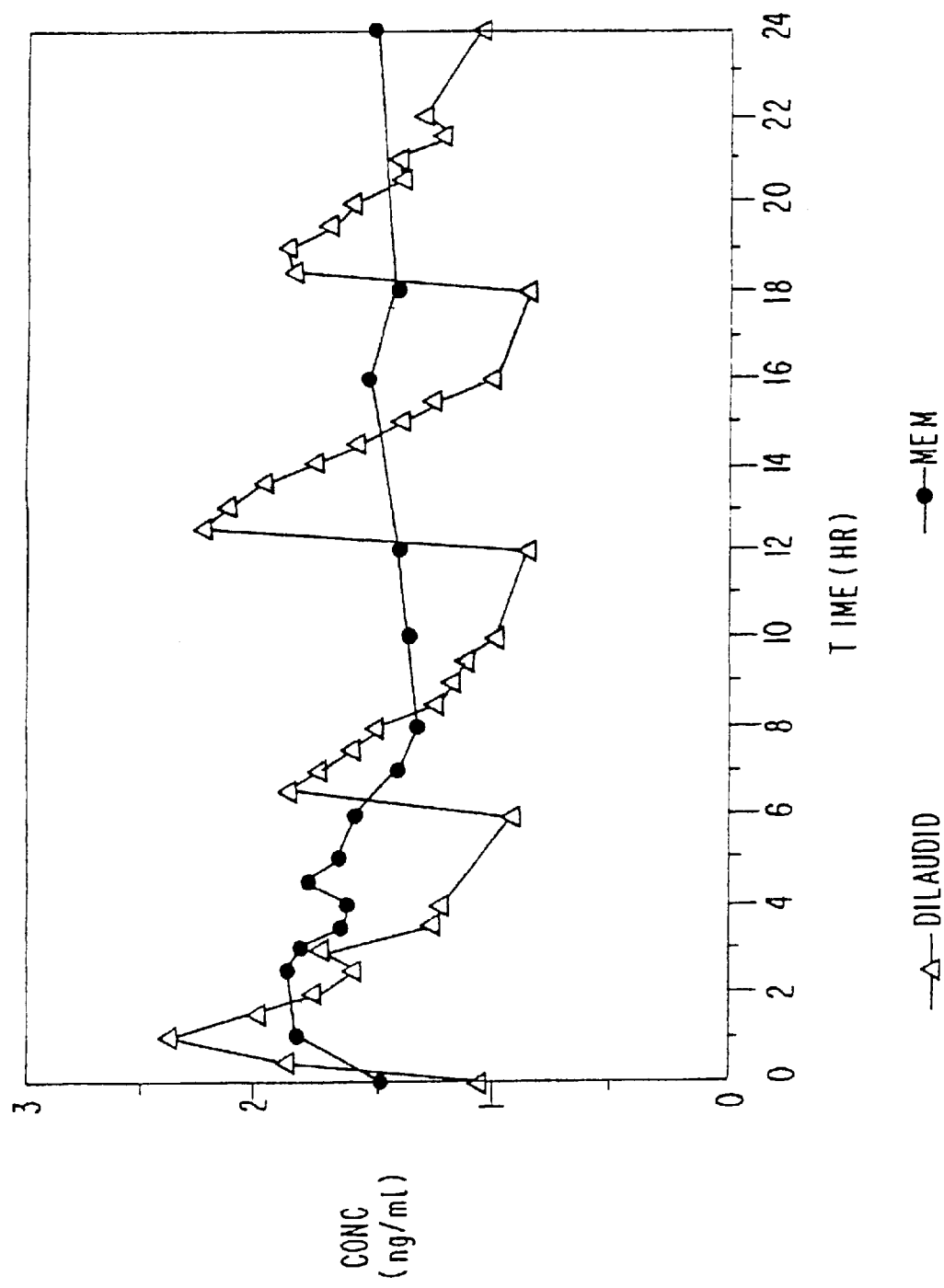
FIG. 16 is a graph of the steady-state plasma hydromorphone concentrations of Example 25 using the capsules of Example 17.

The results are shown graphically in FIG. 16. From this data it can be seen that Example 17 is an ideal product for once-a-day administration for either single dose or multiple dose administration.

EXAMPLE 26

Bioabailability of HH-MEM 8 mg Capsules

To assess bioavailablity and effect of food on hydromorphone MEM capsules, a single dose, three-way crossover study was conducted in 12 normal male volunteers. The subjects received either 8 mg of Dilaudid tablet (immediate release) or 8 mg of HH-MEM (Example 19) Dilaudid tablets were administered after an overnight fast. MEM capsules were administered with our without food. Venous blood samples were taken at predetermined at time points. The plasma hydromorphone concentrations were quantitated using gas chromatography with mass detection (G/MS).

From the data, the following pharmacokinetic parameters were calculated and are set forth in Table 26 below.

TABLE 26

| Treatment | AUC, n · hr/ml | Cmax, n/ml | Tmax, hr |
| --- | --- | --- | --- |
| Example 19, fasted | 15.83 | 0.52 | 5.6 |
| Example 19, fed | 16.55 | 0.65 | 4.1 |
| Dilaudid, fasted | 16.54 | 3.15 | 0.8 |

Figure 17:
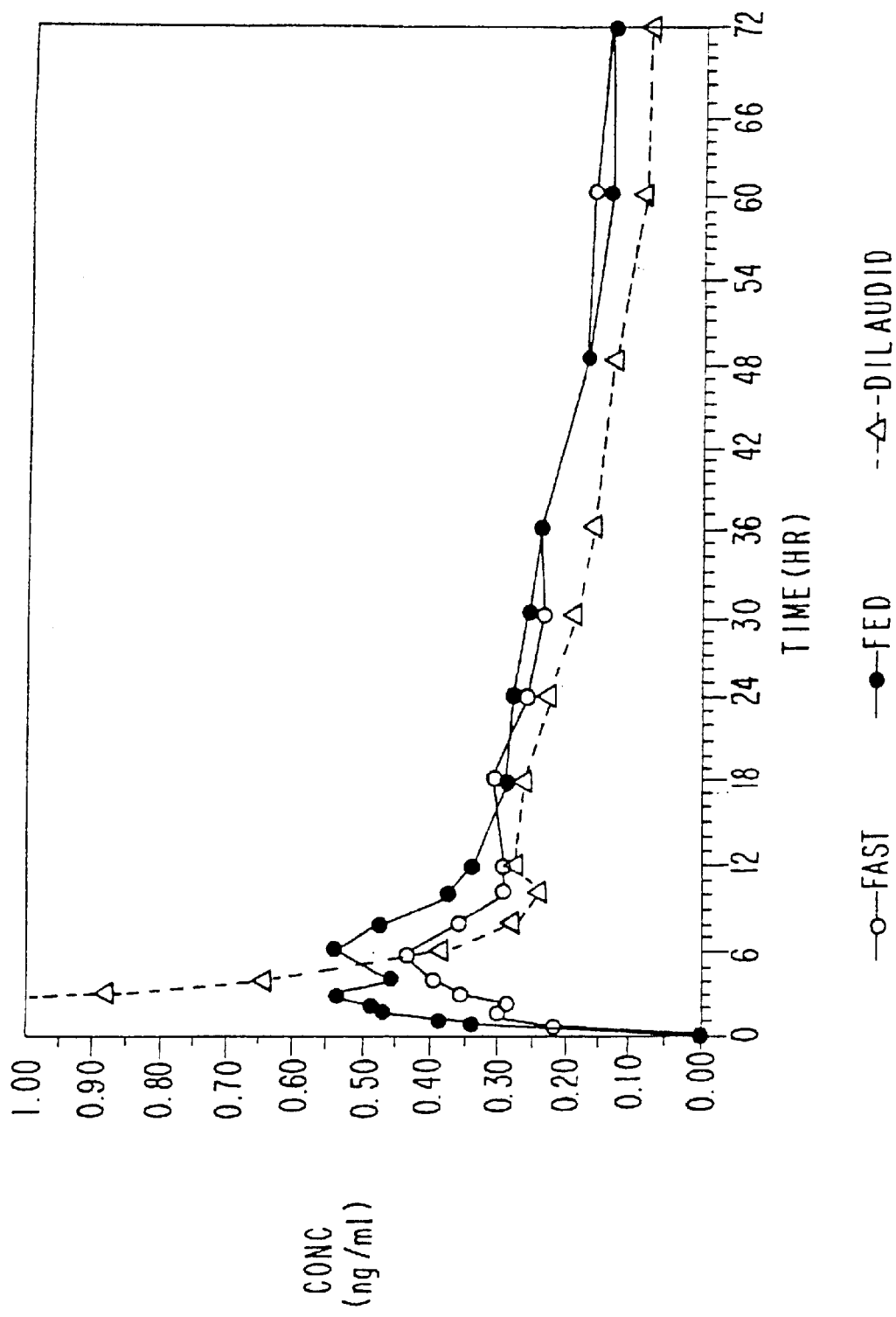
FIG. 17 is a graph of the plasma hydromorphone concentrations of Example 26 using the capsules of Example 19.

From the above data it can be concluded that a once-a-day Hydromorphone product can be produced using other ingredients than are used for Examples 17 and 18. This data is shown graphically in FIG. 17.

EXAMPLE 27

Tramadol HCl 200 mg SR Tablet

The following formula is used to prepare melt extrusion granulation and tablet.

TABLE 27

| Ingredients | Amt (mg)/Tablet | Percentage in Formula |
| --- | --- | --- |
| Tramadol HCl | 200 | 53.4 |
| Eudragit RSPO | 74 | 19.8 |
| Tributyl Citrate | 14.8 | 4.0 |
| Stearyl Alcohol | 74 | 19.8 |
| Talc | 7.4 | 2.0 |
| Magnesium Stearate | 3.8 | 1.0 |
| Total | 374 | 100 |

Granulation Manufacture a. Extruder system description—The twin screw extruder is consisted of a pair of counterrotating screws and a barrel block equipped with heating/cooling zones. The stranded extrudate is congealed on a conveyor belt and cut into pellets of the desirable size.

b. Manufacturing procedure-
1. Blend the drug and all the excipients in a proper mixer.
2. Place the mixture in a powder feeder.
3. Set temperatures of the extruder heating zones to approximately 65° C.
4. Set the extruder screw rotation speed to 40 rpm.
5. Start the feeder and the conveyor.
6. After the excipients are melted and the drug embedded in the molten mixture, the viscous mass is extruded as spaghetti-like strands.
7. The extrudate is congealed and hardened while being carried away on a conveyor belt.
8. The stranded extrudate was cut into pellets of 2 mm in diameter and 2–8 cm in length.

Tabletting

The pellets were milled into granules through a suitable screen. The granulation was blended with talc and magnesium stearate. The mixture was then compressed into capsule-shaped tablets.

Dissolution Method

1. Apparatus—USP Type II (paddle), 100 rpm at 37° C.
2. The tablet was placed in a tablet sinker clip and immersed in each vessel.
3. Media—900 ml pH 6.5 phosphate buffer.
4. Analytical method—High performance liquid chromatography.

The above tablets were founded to have the following dissolution results:

TABLE 27a

| | Time (hr) | | | | | | |
|---|---|---|---|---|---|---|---|
| | 1 | 2 | 4 | 8 | 12 | 18 | 24 |
| Mean % dissolved | 24 | 33 | 45 | 61 | 71 | 82 | 88 |

EXAMPLE 28

Tramadol HCl 200 mg SR Tablet

The following formula is used to prepare melt extrusion granulation and tablet with a slower dissolution profile than Example 27.

TABLE 28

| Ingredients | Amt (mg)/Tablet | Percentage in Formula |
|---|---|---|
| Tramadol HCl | 200 | 44.1 |
| Ethyl cellulose | 110 | 24.3 |
| Tributyl Citrate | 22 | 4.9 |
| Stearyl Alcohol | 110 | 14.3 |
| Talc | 7.4 | 1.6 |
| Magnesium Stearate | 3.4 | 0.8 |
| Total | 453.2 | 100 |

The manufacturing procedure and dissolution method are the same as described in Example 27. Additional dissolution media used include pH 1.2 simulated gastric fluid (SGF) without enzyme, pH 7.5 simulated intestinal fluid (SIF) without enzyme, and pH 4 phosphate buffer.

The above tablets were found to have the following dissolution results:

TABLE 28a

| | Time (hr) | | | | | | |
|---|---|---|---|---|---|---|---|
| Mean % dissolved | 1 | 2 | 4 | 8 | 12 | 18 | 24 |
| SGF | 18 | 26 | 35 | 49 | 59 | 70 | 80 |
| pH4 | 17 | 25 | 34 | 49 | 60 | 73 | 83 |
| pH6.5 | 17 | 23 | 33 | 46 | 57 | 70 | 81 |
| SIF | 17 | 23 | 32 | 45 | 56 | 68 | 78 |

The results show that the dissolution profiles of Tramadol SR tablets in media of different pH values are similar. Based on our experience with similar formula of other opiates, a formula which demonstrates pH independent dissolution profile would provide a consistent drug release profile in vivo without food effect.

The examples provided above are not meant to be exclusive. Many other variations of the present invention would be obvious to those skilled in the art, and are contemplated to be within the scope of the appended claims.

It is claimed:

1. A sustained-release pharmaceutical formulation comprising an extruded blend of a therapeutically active agent, one or more hydrophobic materials selected from the group consisting of alkylcelluloses, acrylic polymers, and mixtures thereof; and one or more hydrophobic fusible carriers having a melting point from about 30° to about 200° C. and selected from the group consisting of natural or synthetic waxes, fatty acids, fatty alcohols, and mixtures thereof, said extruded blend divided into a unit dose containing an effective amount of said therapeutically active agent to render a desired therapeutic effect and providing a sustained-release of said therapeutically active agent for a time period of from about 8 to about 24 hours, said extruded blend being formed by mixing the therapeutically active agent, the one or more hydrophobic materials, and the one or more hydrophobic fusible carriers in an extruder to form said blend and extruding said blend through the extruder.

2. The formulation of claim 1, wherein said extrudate comprises a strand-shaped matrix cut into multi-particulates having a length of from about 0.1 to about 5 mm in length.

3. The formulation of claim 1, wherein said extrudate has a diameter of from about 0.1 to about 5 mm.

4. The formulation of claim 1, wherein said therapeutically active agent is an opioid analgesic or a pharmaceutically acceptable salt thereof.

5. The formulation of claim 4, wherein said opioid analgesic is selected from the group consisting of alfentanil, allylprodine, alphaprodine, anileridine, benzylmorphine, bezitramide, bupernorphine, butorphanol, clonitazene, codeine, cyclazocine, desomorphine, dextromoramide, dexocine, diampromide, dihydrocodeine, dihydromorphine, dimenoxadol, dimepheptanol, dimethylthiambutene, dioxaphetyl, butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levallorphan, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propiram, propoxyphene, sufentanil, tramadol, tilidine, pharmaceutically acceptable salts thereof and mixtures thereof.

6. The extrudate of claim 5 wherein said opioid analgesic is selected from the group consisting of morphine, codeine, hydromorphone, hydrocodone, oxycodone, oxymorphone, dihydrocodeine, dihydromorphine, tramadol, pharmaceutically acceptable salts thereof and mixtures thereof.

7. The formulation of claim 2, wherein a unit dose comprising an effective amount of said multiparticulates to render a therapeutic effect is contained within a gelatin capsule.

8. The formulation of claim 2, wherein a unit dose comprising an effective amount of said multiparticulates to render a therapeutic effect is compressed into a tablet.

9. The formulation of claim 8, wherein said therapeutically active agent is tramadol or a pharmaceutically acceptable salt thereof.

10. The formulation of claim 7 wherein said therapeutically active agent is an opioid analgesic selected from the group consisting of morphine, codeine, hydromorphone, hydrocodone, oxycodone, oxymorphone, dihydrocodeine, dihydromorphine, tramadol, pharmaceutically acceptable salts thereof and mixtures thereof.

11. The formulation of claim 10, which provides an in-vitro release (when assessed by the USP Paddle or Basket Method at 100 prm at 900 ml aqueous buffer (pH between 1.6 and 7.2) at 37° C. from about 1 to about 42.5% opioid released after one hour, from about 5 to about 65% opioid released after 2 hours, from about 15 to about 85% opioid released after 4 hours, from about 20 to about 90% opioid released after 6 hours, from about 35 to about 95% opioid released after 12 hours, from about 45 to about 100% opioid released after 18 hours, and from about 55 to about 100% opioid released after 24 hours, by weight.

12. The formulation of claim 10 which provides a peak plasma level at from about 2 to about 8 hours after oral administration.

13. The formulation of claim 10, which provides a $W_{50}$ from about 4 to about 12 hours.

14. The formulation of claim 10, which provides a rapid rate of initial rise in the plasma concentration of the opioid after oral administration, such that the peak plasma level obtained in-vivo occurs from about 2 to about 8 hours after oral administration.

15. The formulation of claim 10, which provides a rapid rate of initial rise in the plasma concentration of the opioid after oral administration, such that the absorption half-life is from about 1 to about 8 hours after oral administration (in the fasted state).

16. The formulation of claim 10, which provides an in-vitro release (when assessed by the USP Paddle or Basket Method at 100 prm at 900 ml aqueous buffer (pH between 1.6 and 7.2) at 37° C. from about 12.5 to about 42.5% opioid released after one hour, from about 25 to about 65% opioid released after 2 hours, from about 45 to about 85% opioid released after 4 hours, and greater than about 60% opioid released after 8 hours, by weight.

17. A method of preparing a sustained-release pharmaceutical extrudate suitable for oral administration, comprising:

blending in an extruder, a therapeutically active agent together with (1) a hydrophobic material selected from the group consisting of alkylcelluloses, acrylic polymers, and mixtures thereof and (2) a hydrophobic fusible carrier selected from the group consisting of natural or synthetic waxes, fatty acids, fatty alcohols, and mixtures thereof, said retardant material having a melting point between 30–200° C. and being included in an amount sufficient to further slow the release of the therapeutically active agent, heating said blend to a temperature sufficient to soften the mixture sufficiently to extrude the same;

extruding said heated mixture as a strand having a diameter of from 0.1–3 mm; cooling said strand; and dividing said strand to form non-spheroidal multi-particulates of said extrudate having a length from 0.1–5 mm; and dividing said non-spheroidal multi-particulates into unit doses containing an effective amount of said therapeutically active agent, said unit dose providing a sustained-release of said therapeutically active agent for a time period of from about 8 to about 24 hours.

18. The method of claim 17, wherein said therapeutically active agent is an opioid analgesic is selected from the group consisting of alfentanil, allylprodine, alphaprodine, anileridine, benzylmorphine, bezitramide, bupernorphine, butorphanol, clonitazene, codeine, cyclazocine, desomorphine, dextromoramide, dexocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levallorphan, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propiram, propoxyphene, sufentanil, tramadol, tilidine, pharmaceutically acceptable salts thereof and mixtures thereof.

19. The method of claim 17, further comprising containing said unit dose of said multiparticulates within a gelatin capsule.

20. The formulation of claim 1, further comprising a plasticizer.

21. The formulation of claim 1, further comprising a lubricant.

22. The formulation of claim 20, wherein said plasticizer is selected from the group consisting of diethyl phthalate, tributyl citrate, triacetin, and mixtures thereof.

23. The formulation of claim 21, wherein said lubricant is selected from the group consisting of magnesium stearate, stearic acid, talc, and mixtures thereof.

24. The dosage form of claim 6, wherein said opioid analgesic is hydromorphone or a pharmaceutically acceptable salt thereof and the unit dose comprises from about 4 mg to about 64 mg of hydromorphone or a pharmaceutically acceptable salt thereof.

25. The dosage form of claim 6, wherein said opioid analgesic is morphine or a pharmaceutically acceptable salt thereof and the unit dose comprises from about 5 mg to about 800 mg of morphine or a pharmaceutically acceptable salt thereof.

26. The dosage form of claim 6, wherein said opioid analgesic is oxycodone or a pharmaceutically acceptable salt thereof and the unit dose comprises from about 5 mg to about 400 mg of oxycodone or a pharmaceutically acceptable salt thereof.

27. The method of claim 18, further comprising blending a plasticizer with said therapeutically active agent, said hydrophobic material, and said hydrophobic fusible carrier prior to heating said blend.

28. The method of claim 32, wherein said plasticizer is selected from the group consisting of diethyl phthalate, tributyl citrate, triacetin, and mixtures thereof.

29. The method of claim 19, wherein said opioid analgesic is hydromorphone or a pharmaceutically acceptable salt thereof and the unit dose comprises from about 4 mg to about 64 mg of hydromorphone or a pharmaceutically acceptable salt thereof.

30. The method of claim 19, wherein said opioid analgesic is morphine or a pharmaceutically acceptable salt thereof and the unit dose comprises from about 5 mg to about 800 mg of morphine or a pharmaceutically acceptable salt thereof.

31. The method of claim 19, wherein said opioid analgesic is oxycodone or a pharmaceutically acceptable salt thereof and the unit dose comprises from about 5 mg to about 400 mg of oxycodone or a pharmaceutically acceptable salt thereof.

32. The dosage from claim 6, wherein said opioid analgesic hydromorphone or a pharmaceutically acceptable salt thereof and the unit dose comprises from about 4 mg to about 64 mg of hydromorphone or a pharmaceutically acceptable salt thereof.

33. The dosage from claim 6, wherein said opioid analgesic is morphine or a pharmaceutically acceptable salt thereof and wherein said unit dose comprises from about 5 mg to about 800 mg of morphine or a pharmaceutically acceptable salt thereof.

34. The dosage form of claim 6, wherein said opioid analgesic is oxycodone or a pharmaceutically acceptable salt thereof and wherein said unit dose comprises from about 5 mg to about 400 mg of oxycodone or a pharmaceutically acceptable salt thereof.

* * * * *